United States Patent [19]
Sidransky

[11] Patent Number: 5,561,041
[45] Date of Patent: Oct. 1, 1996

[54] NUCLEIC ACID MUTATION DETECTION BY ANALYSIS OF SPUTUM

[75] Inventor: David Sidransky, Baltimore, Md.

[73] Assignee: The Johns Hopkins University School of Medicine, Baltimore, Md.

[21] Appl. No.: 152,313

[22] Filed: Nov. 12, 1993

[51] Int. Cl.$^6$ .............................. C12Q 1/68; C12P 19/34
[52] U.S. Cl. ................. 435/6; 435/91.2; 935/77; 935/78
[58] Field of Search ............ 435/6, 91.1, 91.2; 935/77, 78

[56] References Cited

U.S. PATENT DOCUMENTS 4,683,195  7/1987  Mullis et al. ..................... 435/6

FOREIGN PATENT DOCUMENTS 0390323  10/1990  European Pat. Off. ............. 435/6

OTHER PUBLICATIONS

Affermann et al., Anal Quant Cytol Histol (US) 7(3):218–226 (1985).
Taheda et al., Hum Mutat (US) 2(2):112–117(1993).
Verlaan–de Vries et al., Gene 50:313–320 (1986).

Primary Examiner—Stephanie W. Zitomer
Attorney, Agent, or Firm—Fish & Richardson P.C.

[57] ABSTRACT

Methods for detection of target nucleic acids associated with lung neoplasias in sputum specimens which contain mutations and reagents therefor are described.

19 Claims, 1 Drawing Sheet

SEQUENCE LISTING ( 1 ) GENERAL INFORMATION:

( i i i ) NUMBER OF SEQUENCES: 128

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: K-ras primer ( i x ) FEATURE:
        ( A ) NAME/KEY: CDS
        ( B ) LOCATION: 1..28

( x i ) SEQUENCE DESCRIPTION: SEQ ID NO:1:

AGGAATTCAT GACTGAATAT AAACTTGT 28

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: K-ras primer ( i x ) FEATURE:
        ( A ) NAME/KEY: CDS
        ( B ) LOCATION: 1..30

( x i ) SEQUENCE DESCRIPTION: SEQ ID NO:2:

ATCGAATTCT ATGCATATTA AAACAAGATT 30

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: p53-5S ( i x ) FEATURE:
        ( A ) NAME/KEY: CDS
        ( B ) LOCATION: 1..26

( x i ) SEQUENCE DESCRIPTION: SEQ ID NO:3:

GTAGGAATTC ACTTGTGCCC TGACTT 26

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single ( D ) TOPOLOGY: linear ( i i ) MOLECULE TYPE: DNA (genomic)

( v i i ) IMMEDIATE SOURCE:
          ( B ) CLONE: p53-6AS ( i x ) FEATURE:
          ( A ) NAME/KEY: CDS
          ( B ) LOCATION: 1..27

( x i ) SEQUENCE DESCRIPTION: SEQ ID NO:4:

CATCGAATTC CACTGACAAC CACCCTT 27

( 2 ) INFORMATION FOR SEQ ID NO:5:

( i ) SEQUENCE CHARACTERISTICS:
          ( A ) LENGTH: 27 base pairs
          ( B ) TYPE: nucleic acid
          ( C ) STRANDEDNESS: single
          ( D ) TOPOLOGY: linear ( i i ) MOLECULE TYPE: DNA (genomic)

( v i i ) IMMEDIATE SOURCE:
          ( B ) CLONE: p53-7S ( i x ) FEATURE:
          ( A ) NAME/KEY: CDS
          ( B ) LOCATION: 1..27

( x i ) SEQUENCE DESCRIPTION: SEQ ID NO:5:

GTAGGAATTC CAAGGCGCAC TGGCCTC 27

( 2 ) INFORMATION FOR SEQ ID NO:6:

( i ) SEQUENCE CHARACTERISTICS:
          ( A ) LENGTH: 26 base pairs
          ( B ) TYPE: nucleic acid
          ( C ) STRANDEDNESS: single
          ( D ) TOPOLOGY: linear ( i i ) MOLECULE TYPE: DNA (genomic)

( v i i ) IMMEDIATE SOURCE:
          ( B ) CLONE: p53-8AS ( i x ) FEATURE:
          ( A ) NAME/KEY: CDS
          ( B ) LOCATION: 1..26

( x i ) SEQUENCE DESCRIPTION: SEQ ID NO:6:

ACTGAATTCT TCGTCTCCTC CACCGC 26

( 2 ) INFORMATION FOR SEQ ID NO:7:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( i i ) MOLECULE TYPE: DNA (genomic)

( v i i ) IMMEDIATE SOURCE:
          ( B ) CLONE: K-ras Val12

( i x ) FEATURE:
          ( A ) NAME/KEY: CDS
          ( B ) LOCATION: 1..20

( x i ) SEQUENCE DESCRIPTION: SEQ ID NO:7:

TTGCCTACGC CAACAGCTCC 20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: K-ras Asp12

( i x ) FEATURE:
        ( A ) NAME/KEY: CDS
        ( B ) LOCATION: 1..20

( x i ) SEQUENCE DESCRIPTION: SEQ ID NO:8:

TTGCCTACGC CATCAGCTCC     20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: K-ras Ser12

( i x ) FEATURE:
        ( A ) NAME/KEY: CDS
        ( B ) LOCATION: 1..20

( x i ) SEQUENCE DESCRIPTION: SEQ ID NO:9:

TTGCCTACGC CACTAGCTCC     20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: K-ras Cys12

( i x ) FEATURE:
        ( A ) NAME/KEY: CDS
        ( B ) LOCATION: 1..20

( x i ) SEQUENCE DESCRIPTION: SEQ ID NO:10:

TTGCCTACGC CACAAGCTCC     20

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: p53 His273

( i x ) FEATURE:
    ( A ) NAME/KEY: CDS
    ( B ) LOCATION: 1..18

( x i ) SEQUENCE DESCRIPTION: SEQ ID NO:11:

CACAAACATG CACCTCAA                                        18

( 2 ) INFORMATION FOR SEQ ID NO:12:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: p53 Gly281

( i x ) FEATURE:
        ( A ) NAME/KEY: CDS
        ( B ) LOCATION: 1..17

( x i ) SEQUENCE DESCRIPTION: SEQ ID NO:12:

TGCGCCGGCC TCTCCCA                                        17

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: K-ras WT ( i x ) FEATURE:
        ( A ) NAME/KEY: CDS
        ( B ) LOCATION: 1..20

( x i ) SEQUENCE DESCRIPTION: SEQ ID NO:13:

TTGCCTACGC CACCAGCTCC                                  20

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: p53 WT ( i x ) FEATURE:
        ( A ) NAME/KEY: CDS
        ( B ) LOCATION: 1..18

( x i ) SEQUENCE DESCRIPTION: SEQ ID NO:14:

CCGGTTCATG GCGCCCAT                                      18

( 2 ) INFORMATION FOR SEQ ID NO:15:

( i ) SEQUENCE CHARACTERISTICS:
        ( A ) LENGTH: 16 base pairs (B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..16

(xi) SEQUENCE DESCRIPTION: SEQ ID NO:15:

CACCAGCCCC TCCTGG 16

(2) INFORMATION FOR SEQ ID NO:16:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..18

(xi) SEQUENCE DESCRIPTION: SEQ ID NO:16:

TCTGGGCTGC TTGCATTC 18

(2) INFORMATION FOR SEQ ID NO:17:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..17

(xi) SEQUENCE DESCRIPTION: SEQ ID NO:17:

GCCAACTGCC CAAGACC 17

(2) INFORMATION FOR SEQ ID NO:18:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..17

(xi) SEQUENCE DESCRIPTION: SEQ ID NO:18:

GCCCTGTGTA GCTGTGG 17

(2) INFORMATION FOR SEQ ID NO:19:

(i) SEQUENCE CHARACTERISTICS:
(A) LENGTH: 18 base pairs
(B) TYPE: nucleic acid
(C) STRANDEDNESS: single
(D) TOPOLOGY: linear

33

34

-continued (i i) MOLECULE TYPE: DNA (genomic)

(i x) FEATURE:
  (A) NAME/KEY: CDS
  (B) LOCATION: 1..18

(x i) SEQUENCE DESCRIPTION: SEQ ID NO:19:

GCAGCTGTGA GTTGATTC                                                                                           18

(2) INFORMATION FOR SEQ ID NO:20:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (i i) MOLECULE TYPE: DNA (genomic)

(i x) FEATURE:
    (A) NAME/KEY: CDS
    (B) LOCATION: 1..17

(x i) SEQUENCE DESCRIPTION: SEQ ID NO:20:

TTCCACACAC CCGCCCG                                                                                            17

(2) INFORMATION FOR SEQ ID NO:21:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (i i) MOLECULE TYPE: DNA (genomic)

(i x) FEATURE:
    (A) NAME/KEY: CDS
    (B) LOCATION: 1..16

(x i) SEQUENCE DESCRIPTION: SEQ ID NO:21:

CCCGCCCGTC ACCCGC                                                                                             16

(2) INFORMATION FOR SEQ ID NO:22:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (i i) MOLECULE TYPE: DNA (genomic)

(i x) FEATURE:
    (A) NAME/KEY: CDS
    (B) LOCATION: 1..16

(x i) SEQUENCE DESCRIPTION: SEQ ID NO:22:

GCACCCGCTT CCGCGC                                                                                             16

(2) INFORMATION FOR SEQ ID NO:23:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (i i) MOLECULE TYPE: DNA (genomic)

(i x) FEATURE:
    (A) NAME/KEY: CDS (B) LOCATION: 1..16

(xi) SEQUENCE DESCRIPTION: SEQ ID NO:23:

CCGCGTCCTC GCCATG                                                                                      16

(2) INFORMATION FOR SEQ ID NO:24:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..16

(xi) SEQUENCE DESCRIPTION: SEQ ID NO:24:

CGTCCGCGTC ATGGCC                                                                                      16

(2) INFORMATION FOR SEQ ID NO:25:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..17

(xi) SEQUENCE DESCRIPTION: SEQ ID NO:25:

CGCCATGGAC ATCTACA                                                                                     17

.(2) INFORMATION FOR SEQ ID NO:26:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..17

(xi) SEQUENCE DESCRIPTION: SEQ ID NO:26:

CGCCATGACC ATCTACA                                                                                     17

(2) INFORMATION FOR SEQ ID NO:27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..18

(xi) SEQUENCE DESCRIPTION: SEQ ID NO:27:

ACATGACGTA GGTTGTGA 18

(2) INFORMATION FOR SEQ ID NO:28:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..17

(xi) SEQUENCE DESCRIPTION: SEQ ID NO:28:

CGGAGGTTTT GAGGCGC 17

(2) INFORMATION FOR SEQ ID NO:29:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..17

(xi) SEQUENCE DESCRIPTION: SEQ ID NO:29:

TTGTGAGGCA CTGCCCC 17

(2) INFORMATION FOR SEQ ID NO:30:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..17

(xi) SEQUENCE DESCRIPTION: SEQ ID NO:30:

TTGTGAGGCT CTGCCCC 17

(2) INFORMATION FOR SEQ ID NO:31:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..16

(xi) SEQUENCE DESCRIPTION: SEQ ID NO:31:

AGGCGCTGGC CCCACC 16

(2) INFORMATION FOR SEQ ID NO:32:

( i ) SEQUENCE CHARACTERISTICS:
 ( A ) LENGTH: 16 base pairs
 ( B ) TYPE: nucleic acid
 ( C ) STRANDEDNESS: single
 ( D ) TOPOLOGY: linear ( i i ) MOLECULE TYPE: DNA (genomic)

( i x ) FEATURE:
 ( A ) NAME/KEY: CDS
 ( B ) LOCATION: 1..16

( x i ) SEQUENCE DESCRIPTION: SEQ ID NO:32:

AGGCGCTACC CCCACC                           16

( 2 ) INFORMATION FOR SEQ ID NO:33:

( i ) SEQUENCE CHARACTERISTICS:
 ( A ) LENGTH: 16 base pairs
 ( B ) TYPE: nucleic acid
 ( C ) STRANDEDNESS: single
 ( D ) TOPOLOGY: linear ( i i ) MOLECULE TYPE: DNA (genomic)

( i x ) FEATURE:
 ( A ) NAME/KEY: CDS
 ( B ) LOCATION: 1..16

( x i ) SEQUENCE DESCRIPTION: SEQ ID NO:33:

AGGCGCTTCC CCCACC                           16

( 2 ) INFORMATION FOR SEQ ID NO:34:

( i ) SEQUENCE CHARACTERISTICS:
 ( A ) LENGTH: 17 base pairs
 ( B ) TYPE: nucleic acid
 ( C ) STRANDEDNESS: single
 ( D ) TOPOLOGY: linear ( i i ) MOLECULE TYPE: DNA (genomic)

( i x ) FEATURE:
 ( A ) NAME/KEY: CDS
 ( B ) LOCATION: 1..17

( x i ) SEQUENCE DESCRIPTION: SEQ ID NO:34:

CCCCCACTAT GAGCGCT                          17

( 2 ) INFORMATION FOR SEQ ID NO:35:

( i ) SEQUENCE CHARACTERISTICS:
 ( A ) LENGTH: 16 base pairs
 ( B ) TYPE: nucleic acid
 ( C ) STRANDEDNESS: single
 ( D ) TOPOLOGY: linear ( i i ) MOLECULE TYPE: DNA (genomic)

( i x ) FEATURE:
 ( A ) NAME/KEY: CDS
 ( B ) LOCATION: 1..16

( x i ) SEQUENCE DESCRIPTION: SEQ ID NO:35:

CCCCACCAGG AGCGCT                           16

( 2 ) INFORMATION FOR SEQ ID NO:36:

( i ) SEQUENCE CHARACTERISTICS:
 ( A ) LENGTH: 16 base pairs
 ( B ) TYPE: nucleic acid (C) STRANDEDNESS: single
(D) TOPOLOGY: linear (ii) MOLECULE TYPE: DNA (genomic)

(ix) FEATURE:
    (A) NAME/KEY: CDS
    (B) LOCATION: 1..16

(xi) SEQUENCE DESCRIPTION: SEQ ID NO:36:

CCCCACCGTG AGCGCT 16

(2) INFORMATION FOR SEQ ID NO:37:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 1..16

(xi) SEQUENCE DESCRIPTION: SEQ ID NO:37:

CCCCCACGAT GAGCGC 16

(2) INFORMATION FOR SEQ ID NO:38:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 1..17

(xi) SEQUENCE DESCRIPTION: SEQ ID NO:38:

TCAGCATCGT ATCCGAG 17

(2) INFORMATION FOR SEQ ID NO:39:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 1..19

(xi) SEQUENCE DESCRIPTION: SEQ ID NO:39:

ATCCGAGTGT AAGGAAATT 19

(2) INFORMATION FOR SEQ ID NO:40:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: DNA (genomic)

( i x ) FEATURE:
    ( A ) NAME/KEY: CDS
    ( B ) LOCATION: 1..19

( x i ) SEQUENCE DESCRIPTION: SEQ ID NO:40:

CGAGTGGAAG AAAATTTGC                                                                                  19

( 2 ) INFORMATION FOR SEQ ID NO:41:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..18

( x i ) SEQUENCE DESCRIPTION: SEQ ID NO:41:

TGTGGAGTGT TTGGATGA                                                                                   18

( 2 ) INFORMATION FOR SEQ ID NO:42:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..19

( x i ) SEQUENCE DESCRIPTION: SEQ ID NO:42:

TGGATGACTG AAACACTTT                                                                                  19

( 2 ) INFORMATION FOR SEQ ID NO:43:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..19

( x i ) SEQUENCE DESCRIPTION: SEQ ID NO:43:

ACACTTTTTG ACATAGTGT                                                                                  19

( 2 ) INFORMATION FOR SEQ ID NO:44:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..19

( x i ) SEQUENCE DESCRIPTION: SEQ ID NO:44:

ACACTTTTCC ACATAGTGT 19

( 2 ) INFORMATION FOR SEQ ID NO:45:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..19

( x i ) SEQUENCE DESCRIPTION: SEQ ID NO:45:

CACTTTTCGA CGTAGTGTG 19

( 2 ) INFORMATION FOR SEQ ID NO:46:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..19

( x i ) SEQUENCE DESCRIPTION: SEQ ID NO:46:

TTTTCGACAT ATTGTGGTG 19

( 2 ) INFORMATION FOR SEQ ID NO:47:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..18

( x i ) SEQUENCE DESCRIPTION: SEQ ID NO:47:

ATAGTGTGTT GGTGCCCT 18

( 2 ) INFORMATION FOR SEQ ID NO:48:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..16

( x i ) SEQUENCE DESCRIPTION: SEQ ID NO:48:

GGTGCCCTGT GAGCCG 16

( 2 ) INFORMATION FOR SEQ ID NO:49:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..17

( x i ) SEQUENCE DESCRIPTION: SEQ ID NO:49:

CCGCCTGACG TCTGGTT                      17

( 2 ) INFORMATION FOR SEQ ID NO:50:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..18

( x i ) SEQUENCE DESCRIPTION: SEQ ID NO:50:

TCTGACTGAA CCACCATC                    18

( 2 ) INFORMATION FOR SEQ ID NO:51:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..18

( x i ) SEQUENCE DESCRIPTION: SEQ ID NO:51:

CATCCACTGC AACTACAT                    18

( 2 ) INFORMATION FOR SEQ ID NO:52:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..20

( x i ) SEQUENCE DESCRIPTION: SEQ ID NO:52:

CAACTACATA TGTAACAGTT                  20

( 2 ) INFORMATION FOR SEQ ID NO:53:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..20

( x i ) SEQUENCE DESCRIPTION: SEQ ID NO:53:

ACTACATGTT TAACAGTTCC                                                          20

( 2 ) INFORMATION FOR SEQ ID NO:54:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..20

( x i ) SEQUENCE DESCRIPTION: SEQ ID NO:54:

ACTACATGTG AAACAGTTCC                                                          20

( 2 ) INFORMATION FOR SEQ ID NO:55:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..17

( x i ) SEQUENCE DESCRIPTION: SEQ ID NO:55:

CAGTTCCTCC ATGGGCG                                                              17

( 2 ) INFORMATION FOR SEQ ID NO:56:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..17

( x i ) SEQUENCE DESCRIPTION: SEQ ID NO:56:

CAGTTCCTTC ATGGGCG                                                              17

( 2 ) INFORMATION FOR SEQ ID NO:57:

( i ) SEQUENCE CHARACTERISTICS:
        ( A ) LENGTH: 17 base pairs
        ( B ) TYPE: nucleic acid
        ( C ) STRANDEDNESS: single (D) TOPOLOGY: linear (i i) MOLECULE TYPE: DNA (genomic)

(i x) FEATURE:
 (A) NAME/KEY: CDS
 (B) LOCATION: 1..17

(x i) SEQUENCE DESCRIPTION: SEQ ID NO:57:

CAGTTCCTGG ATGGGCG    17

(2) INFORMATION FOR SEQ ID NO:58:

(i) SEQUENCE CHARACTERISTICS:
 (A) LENGTH: 17 base pairs
 (B) TYPE: nucleic acid
 (C) STRANDEDNESS: single
 (D) TOPOLOGY: linear (i i) MOLECULE TYPE: DNA (genomic)

(i x) FEATURE:
 (A) NAME/KEY: CDS
 (B) LOCATION: 1..17

(x i) SEQUENCE DESCRIPTION: SEQ ID NO:58:

CCTGCATGTG CGGCATG    17

(2) INFORMATION FOR SEQ ID NO:59:

(i) SEQUENCE CHARACTERISTICS:
 (A) LENGTH: 17 base pairs
 (B) TYPE: nucleic acid
 (C) STRANDEDNESS: single
 (D) TOPOLOGY: linear (i i) MOLECULE TYPE: DNA (genomic)

(i x) FEATURE:
 (A) NAME/KEY: CDS
 (B) LOCATION: 1..17

(x i) SEQUENCE DESCRIPTION: SEQ ID NO:59:

GCATGGGCTG CATGAAC    17

(2) INFORMATION FOR SEQ ID NO:60:

(i) SEQUENCE CHARACTERISTICS:
 (A) LENGTH: 17 base pairs
 (B) TYPE: nucleic acid
 (C) STRANDEDNESS: single
 (D) TOPOLOGY: linear (i i) MOLECULE TYPE: DNA (genomic)

(i x) FEATURE:
 (A) NAME/KEY: CDS
 (B) LOCATION: 1..17

(x i) SEQUENCE DESCRIPTION: SEQ ID NO:60:

GCATGGGCGA CATGAAC    17

(2) INFORMATION FOR SEQ ID NO:61:

(i) SEQUENCE CHARACTERISTICS:
 (A) LENGTH: 17 base pairs
 (B) TYPE: nucleic acid
 (C) STRANDEDNESS: single
 (D) TOPOLOGY: linear (i i) MOLECULE TYPE: DNA (genomic)

53 54
-continued ( i x ) FEATURE:
    ( A ) NAME/KEY: CDS
    ( B ) LOCATION: 1..17

( x i ) SEQUENCE DESCRIPTION: SEQ ID NO:61:

GGCGGCATCA ACCGGAG 17

( 2 ) INFORMATION FOR SEQ ID NO:62:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 1..17

( x i ) SEQUENCE DESCRIPTION: SEQ ID NO:62:

GGCATGATCC GGAGGCC 17

( 2 ) INFORMATION FOR SEQ ID NO:63:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 1..18

( x i ) SEQUENCE DESCRIPTION: SEQ ID NO:63:

CATGAACCTG AGGCCCAT 18

( 2 ) INFORMATION FOR SEQ ID NO:64:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 1..18

( x i ) SEQUENCE DESCRIPTION: SEQ ID NO:64:

GCATGAACTG GAGGCCCA 18

( 2 ) INFORMATION FOR SEQ ID NO:65:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 1..18

( x i ) SEQUENCE DESCRIPTION: SEQ ID NO:65:

GCATGAACCA GAGGCCCA    18

( 2 ) INFORMATION FOR SEQ ID NO:66:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..18

( x i ) SEQUENCE DESCRIPTION: SEQ ID NO:66:

AACCGGAGTC CCATCCTC    18

( 2 ) INFORMATION FOR SEQ ID NO:67:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..17

( x i ) SEQUENCE DESCRIPTION: SEQ ID NO:67:

AACCGGAGCC CCATCCT    17

( 2 ) INFORMATION FOR SEQ ID NO:68:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..18

( x i ) SEQUENCE DESCRIPTION: SEQ ID NO:68:

AACCGGATGC CCATCCTC    18

( 2 ) INFORMATION FOR SEQ ID NO:69:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..16

( x i ) SEQUENCE DESCRIPTION: SEQ ID NO:69:

GAACCGGGGG CCCATC    16

(2) INFORMATION FOR SEQ ID NO:70:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..18

(xi) SEQUENCE DESCRIPTION: SEQ ID NO:70:

TCACACTGTA AGACTCCA                    18

(2) INFORMATION FOR SEQ ID NO:71:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..18

(xi) SEQUENCE DESCRIPTION: SEQ ID NO:71:

TCACACTGAA AGACTCCA                    18

(2) INFORMATION FOR SEQ ID NO:72:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..18

(xi) SEQUENCE DESCRIPTION: SEQ ID NO:72:

CACTGGAAGT CTCCAGGT                    18

(2) INFORMATION FOR SEQ ID NO:73:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..18

(xi) SEQUENCE DESCRIPTION: SEQ ID NO:73:

TAATCTACCG GGACGGAA                    18

(2) INFORMATION FOR SEQ ID NO:74:

(i) SEQUENCE CHARACTERISTICS:

(A) LENGTH: 18 base pairs
(B) TYPE: nucleic acid
(C) STRANDEDNESS: single
(D) TOPOLOGY: linear (i i) MOLECULE TYPE: DNA (genomic)

(i x) FEATURE:
(A) NAME/KEY: CDS
(B) LOCATION: 1..18

(x i) SEQUENCE DESCRIPTION: SEQ ID NO:74:

TAATCTACCT GGACGGAA 18

(2) INFORMATION FOR SEQ ID NO:75:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: DNA (genomic)

(i x) FEATURE:
(A) NAME/KEY: CDS
(B) LOCATION: 1..18

(x i) SEQUENCE DESCRIPTION: SEQ ID NO:75:

TCTACTGGTA CGGAACAG 18

(2) INFORMATION FOR SEQ ID NO:76:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: DNA (genomic)

(i x) FEATURE:
(A) NAME/KEY: mat_peptide
(B) LOCATION: 1..18

(x i) SEQUENCE DESCRIPTION: SEQ ID NO:76:

ACTGGGACCG AACAGCTT 18

(2) INFORMATION FOR SEQ ID NO:77:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: DNA (genomic)

(i x) FEATURE:
(A) NAME/KEY: CDS
(B) LOCATION: 1..18

(x i) SEQUENCE DESCRIPTION: SEQ ID NO:77:

GCTTTGAGCT GCGTGTTT 18

(2) INFORMATION FOR SEQ ID NO:78:

(i) SEQUENCE CHARACTERISTICS:
(A) LENGTH: 18 base pairs
(B) TYPE: nucleic acid
(C) STRANDEDNESS: single
(D) TOPOLOGY: linear ( i i ) MOLECULE TYPE: DNA (genomic)

( i x ) FEATURE:
    ( A ) NAME/KEY: CDS
    ( B ) LOCATION: 1..18

( x i ) SEQUENCE DESCRIPTION: SEQ ID NO:78:

GCTTTGAGGA GCGTGTTT 18

( 2 ) INFORMATION FOR SEQ ID NO:79:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
    ( A ) NAME/KEY: CDS
    ( B ) LOCATION: 1..18

( x i ) SEQUENCE DESCRIPTION: SEQ ID NO:79:

TTGAGGTGCT TGTTTGTG 18

( 2 ) INFORMATION FOR SEQ ID NO:80:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
    ( A ) NAME/KEY: CDS
    ( B ) LOCATION: 1..18

( x i ) SEQUENCE DESCRIPTION: SEQ ID NO:80:

TTGAGGTGTG TGTTTGTG 18

( 2 ) INFORMATION FOR SEQ ID NO:81:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
    ( A ) NAME/KEY: CDS
    ( B ) LOCATION: 1..18

( x i ) SEQUENCE DESCRIPTION: SEQ ID NO:81:

TTGAGGTGCA TGTTTGTG 18

( 2 ) INFORMATION FOR SEQ ID NO:82:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:

(A) NAME/KEY: CDS
(B) LOCATION: 1..18

(xi) SEQUENCE DESCRIPTION: SEQ ID NO:82:

TTGAGGTGCC TGTTTGTG    18

(2) INFORMATION FOR SEQ ID NO:83:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..18

(xi) SEQUENCE DESCRIPTION: SEQ ID NO:83:

AGGTGCGTGG TTGTGCCT    18

(2) INFORMATION FOR SEQ ID NO:84:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..18

(xi) SEQUENCE DESCRIPTION: SEQ ID NO:84:

GCGTGTTTAT GCCTGCCT    18

(2) INFORMATION FOR SEQ ID NO:85:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..18

(xi) SEQUENCE DESCRIPTION: SEQ ID NO:85:

GCGTGTTTTT GCCTGCCT    18

(2) INFORMATION FOR SEQ ID NO:86:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..18

(xi) SEQUENCE DESCRIPTION: SEQ ID NO:86:

TTGTGCCTTT CCTGGGAG                                                                                        18

( 2 ) INFORMATION FOR SEQ ID NO:87:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..18

( x i ) SEQUENCE DESCRIPTION: SEQ ID NO:87:

TGCCTGTCTT GGGAGAGA                                                                                        18

( 2 ) INFORMATION FOR SEQ ID NO:88:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..18

( x i ) SEQUENCE DESCRIPTION: SEQ ID NO:88:

TGCCTGTTCT GGGAGAGA                                                                                        18

( 2 ) INFORMATION FOR SEQ ID NO:89:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..18

( x i ) SEQUENCE DESCRIPTION: SEQ ID NO:89:

TGCCTGTCGT GGGAGAGA                                                                                        18

( 2 ) INFORMATION FOR SEQ ID NO:90:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..18

( x i ) SEQUENCE DESCRIPTION: SEQ ID NO:90:

TCCTGGGATA GACCGGCG                                                                                        18

(2) INFORMATION FOR SEQ ID NO:91:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..18

( x i ) SEQUENCE DESCRIPTION: SEQ ID NO:91:

TGGGAGATAC CGGCGCAC                                                          18

(2) INFORMATION FOR SEQ ID NO:92:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..17

( x i ) SEQUENCE DESCRIPTION: SEQ ID NO:92:

GAGAGACCCG CGCACAG                                                        17

(2) INFORMATION FOR SEQ ID NO:93:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..17

( x i ) SEQUENCE DESCRIPTION: SEQ ID NO:93:

GAGAGACGGG CGCACAG                                                        17

(2) INFORMATION FOR SEQ ID NO:94:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..17

( x i ) SEQUENCE DESCRIPTION: SEQ ID NO:94:

GAGAGACTGG CGCACAG                                                        17

(2) INFORMATION FOR SEQ ID NO:95:

( i ) SEQUENCE CHARACTERISTICS:
        ( A ) LENGTH: 17 base pairs ( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..17

( x i ) SEQUENCE DESCRIPTION: SEQ ID NO:95:

AGACCGGCCC ACAGAGG 17

( 2 ) INFORMATION FOR SEQ ID NO:96:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..17

( x i ) SEQUENCE DESCRIPTION: SEQ ID NO:96:

AGACCGGGGC ACAGAGG 17

( 2 ) INFORMATION FOR SEQ ID NO:97:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..16

( x i ) SEQUENCE DESCRIPTION: SEQ ID NO:97:

CCGGCGCCCA GAGGAA 16

( 2 ) INFORMATION FOR SEQ ID NO:98:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..18

( x i ) SEQUENCE DESCRIPTION: SEQ ID NO:98:

GCGCACAAAG GAAGAGAA 18

( 2 ) INFORMATION FOR SEQ ID NO:99:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
    ( A ) NAME/KEY: CDS
    ( B ) LOCATION: 1..18

( x i ) SEQUENCE DESCRIPTION: SEQ ID NO:99:

CACAGAGGGA GAGAATCT                                                              18

( 2 ) INFORMATION FOR SEQ ID NO:100:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..18

( x i ) SEQUENCE DESCRIPTION: SEQ ID NO:100:

ATCTCCGCTA GAAAGGGG                                                        18

( 2 ) INFORMATION FOR SEQ ID NO:101:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..17

( x i ) SEQUENCE DESCRIPTION: SEQ ID NO:101:

GCAAGAAAGG GAGCCTC                                                         17

( 2 ) INFORMATION FOR SEQ ID NO:102:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..17

( x i ) SEQUENCE DESCRIPTION: SEQ ID NO:102:

CTCACCACTA GCTGCCC                                                         17

( 2 ) INFORMATION FOR SEQ ID NO:103:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS ( B ) LOCATION: 1..18

( x i ) SEQUENCE DESCRIPTION: SEQ ID NO:103:

GATGTTCTGA GAGCTGAA 18

( 2 ) INFORMATION FOR SEQ ID NO:104:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..18

( x i ) SEQUENCE DESCRIPTION: SEQ ID NO:104:

GATGTTCCAG AGCTGAAT 18

( 2 ) INFORMATION FOR SEQ ID NO:105:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..18

( x i ) SEQUENCE DESCRIPTION: SEQ ID NO:105:

GGCCTTGAAC TCAAGGAT 18

( 2 ) INFORMATION FOR SEQ ID NO:106:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..16

( x i ) SEQUENCE DESCRIPTION: SEQ ID NO:106:

CTGGGAGACA CCGGCG 16

( 2 ) INFORMATION FOR SEQ ID NO:107:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..17

( x i ) SEQUENCE DESCRIPTION: SEQ ID NO:107:

ACCGGAGGTT CATCCTC                                                                                      17

( 2 ) INFORMATION FOR SEQ ID NO:108:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..19

( x i ) SEQUENCE DESCRIPTION: SEQ ID NO:108:

CATGTGTAAA CAGTTCCTG                                                                                    19

( 2 ) INFORMATION FOR SEQ ID NO:109:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..18

( x i ) SEQUENCE DESCRIPTION: SEQ ID NO:109:

AGCATCTTAA TCCGAGTG                                                                                     18

( 2 ) INFORMATION FOR SEQ ID NO:110:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..17

( x i ) SEQUENCE DESCRIPTION: SEQ ID NO:110:

GTCTGGCCCT CCTCAGC                                                                                      17

( 2 ) INFORMATION FOR SEQ ID NO:111:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..17

( x i ) SEQUENCE DESCRIPTION: SEQ ID NO:111:

GCTGCCCCCC ACCATGA                                                                                      17

( 2 ) INFORMATION FOR SEQ ID NO:112:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 1..15

( x i ) SEQUENCE DESCRIPTION: SEQ ID NO:112:

CCGCGTCGCG CCATG 15

( 2 ) INFORMATION FOR SEQ ID NO:113:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 1..17

( x i ) SEQUENCE DESCRIPTION: SEQ ID NO:113:

AGACCTGCCT GTGCAGC 17

( 2 ) INFORMATION FOR SEQ ID NO:114:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 1..17

( x i ) SEQUENCE DESCRIPTION: SEQ ID NO:114:

CCTGTCCTTG GGAGAGA 17

( 2 ) INFORMATION FOR SEQ ID NO:115:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( v i i ) IMMEDIATE SOURCE:
    ( B ) CLONE: K-ras Val12

( i x ) FEATURE:
    ( A ) NAME/KEY: CDS
    ( B ) LOCATION: 1..20

( x i ) SEQUENCE DESCRIPTION: SEQ ID NO:115:

GGAGCTGTTG GCGTAGGCAA 20

( 2 ) INFORMATION FOR SEQ ID NO:116:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(v i i) IMMEDIATE SOURCE:
        (B) CLONE: K-ras Asp12

(i x) FEATURE:
        (A) NAME/KEY: CDS
        (B) LOCATION: 1..20

(x i) SEQUENCE DESCRIPTION: SEQ ID NO:116:

GGAGCTGATG GCGTAGGCAA                                                                              20

(2) INFORMATION FOR SEQ ID NO:117:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(v i i) IMMEDIATE SOURCE:
        (B) CLONE: K-ras Ser12

(i x) FEATURE:
        (A) NAME/KEY: CDS
        (B) LOCATION: 1..20

(x i) SEQUENCE DESCRIPTION: SEQ ID NO:117:

GGAGCTAGTG GCGTAGGCAA                                                                              20

(2) INFORMATION FOR SEQ ID NO:118:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(v i i) IMMEDIATE SOURCE:
        (B) CLONE: K-ras Cys12

(i x) FEATURE:
        (A) NAME/KEY: CDS
        (B) LOCATION: 1..20

(x i) SEQUENCE DESCRIPTION: SEQ ID NO:118:

GGAGCTTGTG GCGTAGGCAA                                                                              20

(2) INFORMATION FOR SEQ ID NO:119:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(v i i) IMMEDIATE SOURCE:
        (B) CLONE: WT K-ras (i x) FEATURE:
        (A) NAME/KEY: CDS
        (B) LOCATION: 1..20

( x i ) SEQUENCE DESCRIPTION: SEQ ID NO:119:

GGAGCTGGTG GCGTAGGCAA                                    20

( 2 ) INFORMATION FOR SEQ ID NO:120:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: WT p53

( i x ) FEATURE:
        ( A ) NAME/KEY: CDS
        ( B ) LOCATION: 1..18

( x i ) SEQUENCE DESCRIPTION: SEQ ID NO:120:

ATGGGCGCCA TGAACCGG                                      18

( 2 ) INFORMATION FOR SEQ ID NO:121:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: p53 His273

( i x ) FEATURE:
        ( A ) NAME/KEY: CDS
        ( B ) LOCATION: 1..18

( x i ) SEQUENCE DESCRIPTION: SEQ ID NO:121:

TTGAGGTGCA TGTTTGTG                                      18

( 2 ) INFORMATION FOR SEQ ID NO:122:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: p53 Gly281

( i x ) FEATURE:
        ( A ) NAME/KEY: CDS
        ( B ) LOCATION: 1..17

( x i ) SEQUENCE DESCRIPTION: SEQ ID NO:122:

TGGGAGAGGC CGGCGCA                                       17

( 2 ) INFORMATION FOR SEQ ID NO:123:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
    ( B ) CLONE: K-ras probe ( i x ) FEATURE:
    ( A ) NAME/KEY: CDS
    ( B ) LOCATION: 1..28

( x i ) SEQUENCE DESCRIPTION: SEQ ID NO:123:

ACAAGTTTAT ATTCAGTCAT GAATTCCT     28

( 2 ) INFORMATION FOR SEQ ID NO:124:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: K-ras probe ( i x ) FEATURE:
        ( A ) NAME/KEY: CDS
        ( B ) LOCATION: 1..30

( x i ) SEQUENCE DESCRIPTION: SEQ ID NO:124:

AATCTTGTTT TAATATGCAT AGAATTCGAT     30

( 2 ) INFORMATION FOR SEQ ID NO:125:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: p53 probe ( i x ) FEATURE:
        ( A ) NAME/KEY: CDS
        ( B ) LOCATION: 1..26

( x i ) SEQUENCE DESCRIPTION: SEQ ID NO:125:

AAGTCAGGGC ACAAGTGAAT TCCTAC     26

( 2 ) INFORMATION FOR SEQ ID NO:126:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: p53 probe ( i x ) FEATURE:
        ( A ) NAME/KEY: CDS
        ( B ) LOCATION: 1..27

( x i ) SEQUENCE DESCRIPTION: SEQ ID NO:126:

AAGGGTGGTT GTCAGTGGAA TTCGATG     27

( 2 ) INFORMATION FOR SEQ ID NO:127:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: p53 probe ( i x ) FEATURE:
( A ) NAME/KEY: CDS
( B ) LOCATION: 1..27

( x i ) SEQUENCE DESCRIPTION: SEQ ID NO:127:

GAGGCCAGTG CGCCTTGGAA TTCCTAC 27

( 2 ) INFORMATION FOR SEQ ID NO:128:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: p53 probe ( i x ) FEATURE:
( A ) NAME/KEY: CDS
( B ) LOCATION: 1..26

( x i ) SEQUENCE DESCRIPTION: SEQ ID NO:128:

GCGGTGGAGG AGACGAAGAA TTCAGT 26

NUCLEIC ACID MUTATION DETECTION BY ANALYSIS OF SPUTUM

This work was supported by a grant from the National Cancer Institute (NCI Grant #1P50 CA58184-01). The United States Government may retain certain rights in the invention.

BACKGROUND OF THE INVENTION

1. Field of the Invention

This invention relates to a method of detecting a target nucleic acid in sputum and reagents useful therein.

2. Background

An increasing body of evidence implicates somatic mutations as causally important in the induction of human cancers. These somatic mutations may accumulate in the genomes of previously normal cells, some of which may then demonstrate the phenotypes associated with malignant growth. Such oncogenic mutations may include a number of different types of alterations in DNA structure, including deletions, translocations and single nucleotide alterations. The latter, also known as point mutations, may frequently be involved in carcinogenesis, in that a variety of mutagenic chemicals induce such mutations. In addition, such mutations may occur spontaneously as a result of mistakes in DNA replication.

Advances in recombinant DNA technology have led to the discovery of normal cellular genes (proto-oncogenes and tumor suppressor genes) which control growth, development, and differentiation. Under certain circumstances, regulation of these genes is altered and cause normal cells to assume neoplastic growth characteristics. There are over 40 known proto-oncogenes and suppressor genes to date, which fall into various categories depending on their functional characteristics. These include, (1) growth factors and growth factor receptors, (2) messengers of intracellular signal transduction pathways, for example, between the cytoplasm and the nucleus, and (3) regulatory proteins influencing gene expression and DNA replication.

Point mutations have been directly implicated in the causation of many human tumors. Some tumors carry oncogenes of the ras gene family, which differ from their normal cellular counterpart proto-oncogenes by the presence of a point mutation at one of a limited number of sites in these genes. Similarly, point mutations in critical regions of tumor suppressor genes, such as p53, are often detected in tumor cells. These mutations represent qualitative changes in the tumor cell genome which distinguish these cells from normal cells and provide a basis for diagnosis of the genetic origin of a tumor under study. Identification of the mutations that have created active oncogenes may provide important diagnostic and prognostic clues for tumor development. For example, a number of mutations have been found to alter the 12th codon of the ras oncogenes, causing replacement of a normally present glycine by any of a number of alternative amino acid residues. Such amino acid substitutions create a potent transforming allele. Thus, the presence of a particular nucleotide substitution may be a strong determinant of the behavior of the tumor cell (e.g., its rate of growth, invasiveness, etc.). As a result, DNA probes for oncogene mutations have promise as diagnostic reagents in clinical oncology.

Among the various types of neoplasms, a number of those which are found in the lungs are associated with oncogenic mutations. Lung cancer is the leading cause of cancer related deaths in Western countries. The prognosis for patients with lung cancer is primarily dependent on the stage of the tumor at the time of clinical diagnosis. Currently, only 25 to 40 percent of all lung tumors are considered resectable at the time of initial assessment. Patients diagnosed early with stage I tumors have a 40–70% survival following surgical resection. An attempt at lung cancer screening through the use of tri-annual sputum cytology and annual chest x-ray has proven inadequate for the early detection of lung cancer. Alternatively, the finding that tumors progress through a series of well-defined genetic changes, including point mutations in oncogenes, has stimulated efforts to develop additional, non-invasive tests that could more reliably detect neoplasms of the lung, such attempts have failed. The present invention addresses this need.

SUMMARY OF THE INVENTION

The present invention arose from the unexpected finding that nucleic acid having a mutant nucleotide sequence associated with lung neoplasia is present in detectable levels in sputum specimens from patients with lung neoplasia.

As a consequence of this discovery, the present invention represents a significant advance over such techniques as tissue biopsy by providing a non-invasive, rapid, and accurate method for detecting mutant nucleotide sequences associated with lung neoplasia. The DNA amplification based approach of the invention can identify one cell carrying a mutant gene among a large excess (greater than 10,000) of normal cells. Based on this finding, it is now possible to detect various other target nucleic acids associated with other disease states.

The present invention provides a method which can be used as an adjunct to cytopathology, to screen high-risk populations and to monitor high risk patients undergoing chemoprevention or chemotherapy.

DETAILED DESCRIPTION OF THE INVENTION

Figure 1:
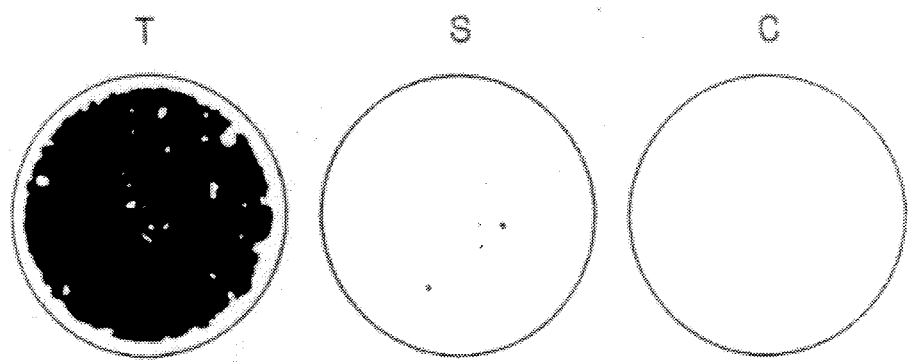
FIG. 1 shows gene mutations in sputum. Clones with a PCR insert from the p53 gene hybridized to an oligomer probe specific for the codon 273 Arg->His mutation in the patient's (L4) tumor (T), fewer clones hybridized to the same probe in the patient's sputum (S) and no clones hybridized to the probe in a control sputum from a Patient (L15) without a p53 gene mutation in the patient's primary lung cancer (C).

The present invention relates to a method of detecting a nucleic acid having a mutant nucleotide sequence present in sputum, wherein the presence of the altered nucleic acid sequence is associated with neoplasia of the lung.

In its broadest sense, the present invention allows the detection of any target nucleic acid sequence of diagnostic or therapeutic relevance, where the target nucleic acid sequence is present in sputum. Thus, the target nucleotide sequence may be, for example, a mutant nucleotide, a restriction fragment length polymorphism (RFLP), a nucleotide deletion, a nucleotide substitution, or any other mammalian nucleic acid sequence of interest.

In one embodiment, the method of the invention is applicable for detection of mutant nucleotide sequences associated with benign as well as malignant neoplasias. In a preferred embodiment neoplasia of the lung is detected, although the method can be used to detect any neoplastic mutant nucleotide sequence, regardless of origin, as long as the sequence is detectably present in sputum. For example, head and neck cancers shed cancer cells into sputum and can be detected.

Numerous nucleic acids having mutant nucleotide sequences that produce an abnormal gene product are known to be associated with various neoplasias. Among the most common mutant nucleotide sequences are oncogenes and tumor suppressor genes, such as the K-ras mutant oncogene, mutated in colon cancer (MCC), deleted in colon cancer (DCC), adenomatous polyposis coli (APC), familial adenomatous polyposis coli (FAP) and p53. Of special significance in the present invention is the detection of the K-ras mutant oncogene and the p53 tumor suppressor gene (Vogelstein, *Nature*, 348:681, 1990).

In order to analyze sputum specimens according to the method of the invention, it is preferable to enrich for epithelial cells present in the specimen. This may be accomplished by mixing the sample with an epithelial cell specific monoclonal antibody, such as EBA-1 or Ber-Ep$_4$ (*Can. Res.* 53:3455, 1993) available from Dakopatts, Gestrop Denmark.) Other epithial cell specific antibodies will be known to those of skill in the art.

Amino acids referred to herein may be identified according to the following three-letter or one-letter abbreviations:

| Amino Acid | Three-Letter Abbreviation | One-Letter Abbreviation |
|---|---|---|
| L-Alanine | Ala | A |
| L-Arginine | Arg | R |
| L-Asparagine | Asn | N |
| L-Aspartic Acid | Asp | D |
| L-Cysteine | Cys | C |
| L-Glutamine | Gln | Q |
| L-Glutamic Acid | Glu | E |
| L-Glycine | Gly | G |
| L-Histidine | His | H |
| L-Isoleucine | Ile | I |
| L-Leucine | Leu | L |
| L-Lysine | Lys | K |
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |

When it is desired to amplify the mutant nucleotide sequence before detection, this can be accomplished using oligonucleotide(s) which are primers for amplification. These unique oligonucleotide primers are based upon identification of the flanking regions contiguous with the mutant nucleotide sequence and are capable of substantially hybridizing with the flanking regions so that amplification can proceed. For example, in the case of K-ras, these oligonucleotide primers comprise sequences such as nucleotide sequence 5'-AGGAATTCATGACTGAATATAAACTTGT-3' (SEQ. ID NO. 1 ) and/or 5'-ATCGAATTCTATGCATAT-TAAAACAAGATT-3' (SEQ. ID NO. 2) and sequences complementary thereto. In the case of p53, the oligonucleotide primers comprise sequences which are capable of hybridizing with the flanking nucleotide sequence, wherein the primers are 5'-GTAGGAATTCACTTGTGCCCTGACTT-3' (SEQ. ID NO. 3) and 5'-CATCGAATTCCACTGACAACCACCCTT-3' (SEQ. ID NO. 4) (exons 5–6) and 5'-GTAGGAATTCCAAGGCGCACTGGCCTC-3' (SEQ. ID NO. 5) and 5'-ACTGAATTCTTCGTCTCCTCCACCGC-3' (SEQ. ID NO. 6) for exons 7–8, and sequences complementary thereto.

The primers which can be used according to the method of the invention embrace oligonucleotides of sufficient length and appropriate sequence so as to provide specific initiation of polymerization of a significant number of nucleic acid molecules containing the target nucleic acid. In this manner, it is possible to selectively amplify the specific target nucleic acid sequence containing the nucleic acid of interest. Specifically, the term "primer" as used herein refers to a sequence comprising two or more deoxyribonucleotides or ribonucleotides, preferably at least eight, which sequence is capable of initiating synthesis of a primer extension product, which is substantially complementary to a target nucleic acid strand. The oligonucleotide primer typically contains 15–22 or more nucleotides, although it may contain fewer nucleotides.

Experimental conditions conducive to synthesis include the presence of nucleoside triphosphates and an agent for polymerization, such as DNA polymerase, and a suitable temperature and pH. The primer is preferably single stranded for maximum efficiency in amplification but may be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition.

Primers used according to the method of the invention are designed to be "substantially" complementary to each strand of target nucleotide sequence to be amplified. Substantially complementary means that the primers must be sufficiently complementary to hybridize with their respective strands under conditions which allow the agent for polymerization to function. In other words, the primers should have sufficient complementarty with the flanking sequences to hybridize therewith and permit amplification of the nucleotide sequence. Preferably, the 3' terminus of the primer that is extended has perfectly base paired complementarity with the complementary flanking strand.

Oligonucleotide primers used according to the invention are employed in any amplification process that produces increased quantities of target nucleic acid. Typically, one primer is complementary to the negative (−) strand of the mutant nucleotide sequence and the other is complementary to the positive (+) strand. Annealing the primers to denatured nucleic acid followed by extension with an enzyme, such as the large fragment of DNA Polymerase I (Klenow) or Taq DNA polymerase and nucleotides results in newly synthesized + and −strands containing the target nucleic acid. Because these newly synthesized nucleic acids are also templates, repeated cycles of denaturing, primer annealing, and extension results in exponential production of the region (i.e., the target mutant nucleotide sequence) defined by the primer. The product of the amplification reaction is a discrete nucleic acid duplex with termini corresponding to the ends of the specific primers employed. Those of skill in the art will know of other amplification methodologies which can also be utilized to increase the copy number of target nucleic acid.

The oligonucleotide primers for use in the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters*, 2.2:1859–1862, 1981). One method for synthesizing oligonucleotides on a modified solid support is described in U.S. Pat. No. 4,458,066. One method of amplification which can be used according to this invention is the polymerase chain reaction (PCR) described in U.S. Pat. Nos. 4,683,202 and 4,683,195.

Any sputum specimen nucleic acid, in purified or nonpurified form, can be utilized as the starting nucleic acid or acids, provided it contains, or is suspected of containing, the specific nucleic acid sequence containing the target nucleic acid. Thus, the process may employ, for example, DNA or RNA, including messenger RNA, wherein DNA or RNA may be single stranded or double stranded. If RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The mutant nucleotide sequence to be amplified, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

Where the target mutant nucleotide sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means; the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (*CSH-Quantitative Biology*, 43:63, 1978) and techniques for using RecA are reviewed in C. Radding (*Ann. Rev. Genetics*, 16:405–437, 1982).

If the nucleic acid containing the target nucleic acid to be amplified is single stranded, its complement is synthesized by adding one or two oligonucleotide primers. If a single primer is utilized, a primer extension product is synthesized in the presence of primer, an agent for polymerization, and the four nucleoside triphosphates described below. The product will be complementary to the single-stranded nucleic acid and will hybridize with a single-stranded nucleic acid to form a duplex of unequal length strands that may then be separated into single strands to produce two single separated complementary strands.

Alternatively, two primers may be added to the single-stranded nucleic acid and the reaction carried out as described.

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7–9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

In some amplification embodiments, the substrates, for example, the deoxyribonucleotide triphosphates dATP, dCTP, dGTP, and dTTP, are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, *E. coli* DNA polymerase I, Taq polymerase, Klenow fragment of *E. coli* DNA polymerase I, T4 DNA polymerase, other available DNA polymerases, polymerase muteins, reverse transcriptase, ligase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each mutant nucleotide strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above. In any event, the method of the invention is not to be limited to the embodiments of amplification which are described herein.

The newly synthesized mutant nucleotide strand and its complementary nucleic acid strand will form a double-stranded molecule under hybridizing conditions described above and this hybrid is used in subsequent steps of the process.

In the next step, the newly synthesized double-stranded molecule is subjected to denaturing conditions using any of the procedures described above to provide single-stranded molecules.

The above process is repeated on the single-stranded molecules. Additional agent for polymerization, nucleosides, and primers may be added, if necessary, for the reaction to proceed under the conditions prescribed above. Again, the synthesis will be initiated at one end of each of the oligonucleotide primers and will proceed along the single strands of the template to produce additional nucleic acid. After this step, half of the extension product will consist of the specific nucleic acid sequence bounded by the two primers.

The steps of denaturing and extension product synthesis can be repeated as often as needed to amplify the target mutant nucleotide sequence to the extent necessary for detection. The amount of the mutant nucleotide sequence produced will accumulate in an exponential fashion.

The amplified product may be detected by analyzing it by Southern blots without using radioactive probes. In such a process, for example, a small sample of DNA containing a very low level of mutant nucleotide sequence is amplified, and analyzed via a Southern blotting technique. The use of non-radioactive probes or labels is facilitated by the high level of the amplified signal.

Nucleic acids having a mutation detected in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad. Sci USA*, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988). Thus, in a preferred embodiment where the mutant nucleotide sequence to be detected is K-ras, a hybridization probe is utilized which is capable of hybridizing with mutant nucleotide sequences comprising 5'-TTGCCTACGCCAACAGCTCC-3' ($Val^{12}$) (SEQ. ID NO. 7), 5'-TTGCCTACGCCATCAGCTCC-3' ($Asp^{12}$) (SEQ. ID NO. 8), 5'-TTGCCTACGCCAC-TAGCTCC-3' ($Ser^{12}$) (SEQ. ID NO. 9), or 5'-TTGC-CTACGCCACAAGCTCC-3' ($Cys^{12}$) (SEQ. ID NO. 10) and sequences complementary thereto. Where the mutant nucleotide sequence to be detected is p53, a hybridization probe is utilized which is capable of hybridizing with mutant nucleotide sequences comprising 5'-CACAAACATGCAC-CTCAA-3' ($His^{273}$) (SEQ. ID NO. 11) or 5'-TGCGCCG-GCCTCTCCCA-3' ($Gly^{281}$) (SEQ. ID NO. 12) and sequences complementary thereto. The wild type K-ras and wild type p53 are detected by hybridizing with nucleotide probes which hybridize with nucleotide sequences comprising 5'-TTGCCTACGCCACCAGCTCC-3' (SEQ. ID NO. 13) and 5'-CCGGTTCATGGCGCCCAT-3' (SEQ. ID NO. 14); respectively.

In an embodiment of the invention, purified nucleic acid fragments containing intervening sequences or oligonucleotide sequences of 10–50 base pairs are radioactively labelled. The labelled preparations are used to probe nucleic acid from sputum by the Southern hybridization technique. Nucleotide fragments from sputum, before or after amplification, are separated into fragments of different molecular masses by gel electrophoresis and transferred to filters which bind nucleic acid. After exposure to the labelled probe, which will hybridize to nucleotide fragments containing target nucleic acid sequences, binding of the radioactive probe to target nucleic acid fragments is identified by autoradiography (see *Genetic Engineering*, 1, ed. Robert Williamson, Academic Press, (1981), 72–81). Alternatively, nucleic acid from sputum can be bound directly to filters to which the radioactive probe selectively binds nucleic acids having the sequence of interest specific sequences and the degree of binding is quantitated by directly counting the radioactive emissions. Where the target nucleic acid is not amplified, detection using an appropriate hybridization probe may be performed directly on the separated mammalian nucleic acid. In those instances where the target nucleic acid is amplified, detection with the appropriate hybridization probe would be performed after amplification.

The probes of the present invention can be used for examining the distribution of the specific fragments detected, as well as the quantitative (relative) degree of binding of the probe for determining the occurrence of specific strongly binding (hybridizing) sequences, thus indicating the likelihood for an individual to be at low risk or high risk for neoplastic disease, such as a lung carcinoma. Further cloning allows specific evaluation of the number of mutant nucleotides (i.e., mutant cells) allowing a precise estimate of risk to develop neoplastic disease.

For the most part, the probe will be labelled with an atom or inorganic radical, most commonly using radionuclides, but also perhaps heavy metals. Conveniently, a radioactive label may be employed. Radioactive labels include $^3P$, $^{125}I$, $^3H$, $^{14}C$, or the like. Any radioactive label may be employed which provides for an adequate signal and has sufficient half-life. Other labels include ligands, which can serve as a specific binding pair member for a labelled ligand, and the like. A wide variety of labels have been employed in immunoassays which can readily be employed in the present assay. The choice of the label will be governed by the effect of the label on the rate of hybridization and binding of the probe to mutant nucleotide sequence. It will be necessary that the label provide sufficient sensitivity to detect the amount of mutant nucleotide sequence available for hybridization. Other considerations will be ease of synthesis of the probe, readily available instrumentation, ability to automate, convenience, and the like.

The manner in which the label is bound to the probe will vary depending upon the nature of the label. For a radioactive label, a wide variety of techniques can be employed. Commonly employed is nick translation with an a $^{32}P$-dNTP or terminal labeling with radioactive $^{32}P$ employing $\gamma^{32}P$-ATP and T4 polynucleotide kinase. Alternatively, nucleotides can be synthesized where one or more of the elements present are replaced with a radioactive isotope, e.g., hydrogen with tritium. If desired, complementary labelled strands can be used as probes to enhance the concentration of hybridized label.

Where other radionuclide labels are involved, various linking groups can be employed. A terminal hydroxyl can be esterified, with inorganic acids, (e.g., $^{32}P$ phosphate), or $^{14}C$ organic acids, or else esterified to provide linking groups to the label. Alternatively, intermediate bases may be substituted with activatable linking groups which can then be linked to a label.

Enzymes of interest as reporter groups will primarily be hydrolases, particularly esterases and glycosidases, or oxidoreductases, particularly peroxidases. Fluorescent compounds include fluorescein and its derivatives, rhodamine and its derivatives, dansyl, umbelliferone, and so forth. Chemiluminescers include luciferin, and 2, 3-dihydrophthalazinediones (e.g., luminol).

The probe can be employed for hybridizing to a nucleotide sequence affixed to a water insoluble porous support. Depending upon the source of the nucleic acid, the manner in which the nucleic acid is affixed to the support may vary. Those of ordinary skill in the art know, or can easily ascertain, different supports which can be used in the method of the invention.

Any mammalian cells present in sputum are treated to liberate their nucleic acid. The target sequences containing mutant nucleotides are amplified by PCR or other aforementioned techniques. The amplified nucleic acid from a sputum specimen is spotted or spread onto a filter to provide a plurality of individual portions. The filter is an inert porous solid support (e.g., nitrocellulose). The lysing and denaturation of nucleic acid, as well as the subsequent washings, can be achieved with an appropriate solution for a sufficient time to lyse the cells and denature the nucleic acid. For lysing, chemical lysing will conveniently be employed, as described previously for the sputum lysis buffer. Other denaturation agents include elevated temperatures, organic reagents (e.g., alcohols, amides, amines, ureas, phenols and sulfoxides) or certain inorganic ions (e.g., thiocyanate and perchlorate).

In a preferred embodiment, the amplified nucleic acid containing the mutant nucleotide is be cloned into a vector (e.g., plasmid, cosmid, bacteriophage) utilizing the 5' restriction sites contained within the amplification primers. Each clone contains one copy of the amplified target sequence. The clone is transferred to filters as described above, followed by denaturation. Hybridization with an oligonucleotide/specific for the mutant nucleotide allows the detection of one mutant nucleotide among 10,000 normal nucleotides which differ at a single base pair.

After denaturation, the filter is washed in an aqueous buffered solution, such as Tris, generally at a pH of about 6 to 8, usually 7. One or more washings may be involved, conveniently using the same procedure as employed for the lysing and denaturation. After the lysing, denaturing, and washes have been accomplished, the nucleic acid spotted filter is dried at an elevated temperature, generally from about 50° C. to 70° C. Under this procedure, the nucleic acid is fixed in position and can be assayed with the probe when convenient.

Pre-hybridization may be accomplished by incubating the filter at a mildly elevated temperature for a sufficient time with the hybridization solution without the probe to thoroughly wet the filter. Various hybridization solutions may be employed, comprising from about 20% to 60% volume, preferably 30%, of an inert polar organic solvent. A common hybridization solution employs about 50% formamide, about 0.5 to 1M sodium chloride, about 0.05 to 0.1M sodium citrate, about 0.05 to 0.2% sodium dodecylsulfate, and minor amounts of EDTA, ficoll (about 300–500 kD), polyvinylpyrrolidone, (about 250–500 kD) and serum albumin. Also included in the hybridization solution will generally be from about 0.5 to 5 mg/ml of sonicated denatured DNA (e.g., calf thymus or salmon sperm) and optionally from about 0.5 to 2% wt/vol glycine. Other additives may also be included, such as dextran sulfate of from about 100 to 1,000 kD and in an amount of from about 8 to 15 weight percent of the hybridization solution.

The particular hybridization technique is not essential to the invention. Other hybridization techniques are described by Gall and Pardue, *Proc. Natl. Acad. Sci.* 63:378, 1969; and John, et al., *Nature*, 223:582, 1969. As improvements are made in hybridization techniques they can readily be applied in the method of the invention.

The amount of labelled probe which is present in the hybridization solution will vary widely, depending upon the nature of the label, the amount of the labelled probe which can reasonably bind to the filter, and the stringency of the hybridization. Generally, substantial excess over stoichiometric concentrations of the probe will be employed to enhance the rate of binding of the probe to the fixed target nucleic acid.

Various degrees of stringency of hybridization may be employed. The more severe the conditions, the greater the complementarily that is required for hybridization between the probe and the single stranded target nucleic acid sequence for duplex formation. Severity can be controlled by temperature, probe concentration, probe length, ionic strength, time, and the like. Conveniently, the stringency of hybridization is varied by changing the polarity of the reactant solution by manipulating the concentration of formamide in the range of 20% to 50%. Temperatures employed will normally be in the range of about 20° C. to 80° C., usually 30° C. to 75° C. (see, generally, *Current Protocols in Molecular Biology*, Ausubel, ed., Wiley & Sons, 1989).

After the filter has been contacted with a hybridization solution at a moderate temperature for a period of time sufficient to allow hybridization to occur, the filter is then introduced into a second solution having analogous concentrations of sodium chloride, sodium citrate and sodium dodecylsulfate as provided in the hybridization solution. The time for which the filter is maintained in the second solution may vary from five minutes to three hours or more. The second solution determines the stringency, dissolving cross duplexes and short complementary sequences. After rinsing the filter at room temperature with dilute sodium citrate-sodium chloride solution, the filter may now be assayed for the presence of duplexes in accordance with the nature of the label. Where the label is radioactive, the filter is dried and exposed to X-ray film.

The label may also be labeled with a fluorescence moiety which can then be probed with a specific antifluorescence antibody. Conjugated to this antibody is horseradish peroxidase enzyme, for example, able to catalyze a chemiluminescent reaction. Production of light can then be seen on rapid exposure to film.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method.

For example, one of the container means may comprise a hybridization probe which is or can be detectably labelled. A second container may comprise a sputum/epithelial cell lysis buffer. The kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radionuclide label.

The above disclosure generally describes the present invention. A more complete understanding can be obtained by reference to the following specific examples which are provided herein for purposes of illustration only and are not intended to limit the scope of the invention.

EXAMPLES

The Johns Hopkins Lung Project (JHLP) developed an archive of sputum specimens during a randomized trial of lung cancer screening (1974–1982). Fifteen patients from that trial went on to develop adenocarcinoma of the lung. The primary lung carcinomas from 10 of these 15 patients contained either a ras or a p53 gene mutation. Using a PCR-based assay, stored sputum samples obtained prior to clinical diagnosis were examined for the presence of these oncogene mutations. In eight out of ten patients, the identical mutation identified in the primary tumor was also detected in at least one sputum sample. The earliest detection of a clonal population of cancer cells in sputum was in a sample obtained more than a year prior to clinical diagnosis. These results provide the basis for a novel approach for detection of lung cancer based on the evolving molecular genetics of this disease.

EXAMPLE 1

PROTOCOL FOR SPUTUM DETECTION

A. DNA PREPARATION: Two to 3 ml of stored sputum (in normal saline as fixative), were placed in 50 ml tubes. The tubes were spun at 1000× g in a Beckman model TJ-6 centrifuge for 15 minutes. The supernatant was decanted and 5 ml phosphate buffered saline (PBS) was added. The tubes were spun at 1000× g in a Beckman model T J-6 centrifuge for 15 minutes and decanted once again. One ml 5 ng/ul proteinase K, 1% SDS solution was added and the tubes were vortexed well. The tubes were then incubated in a water bath at 60° C. for 4–6 hours. The digested sputum was transferred to a 5 ml VACUTAINER (Becton-Dickenson). One ml PC-9 (phenol chloroform equilibrated with Tris at pH 9) was added and the tube was vortexed for 1 minute before spinning at 2500 rpm for 15 minutes using a Hermle Z360 K centrifuge. The supernatant was removed to a new VACUTAINER and the above last step was repeated one more time.

The supernatant was then transferred to a new plastic tube and 330 ul 10M ammonia acetate, 2 ul glycogen, and 3.3 ml 200 proof ethanol were added. The tube was vortexed well and spun at 6000 rpm for 1 hour using a Hermle Z360 K centrifuge. The supernatant was decanted and 3.3 ml 70% Ethanol was added. The tube was spun in the above condition for 2 minutes and the tube was decanted again. The resulting pellet was dried in a HETOVAC (vacuum drier). The pellet was then resuspended in 100 ul of distilled water. The sample was kept at 4° C.

An alternative method for enrichment of malignant epithelial cells and elimination of non-epithelial cells in the sputum, prior to PCR, is as follows. Sputum cells are were isolated by centrifugation at 1,000× g. Cells were washed twice in HBSS with 2% fetal calf serum (FCS) and resuspended in 1 ml. The cell suspension was cooled on ice and 20 ug/ml of a monoclonal antibody with specificity for epithelial cells, EBA-1 (other antibodies with specificity for epithelial cells would be equally effective) was added to the cell suspension and incubated on ice for one hour. The cells were washed twice in cold (2°–8° C.) HBSS with 2% FCS. The cells were resuspended in cold HBSS/2% FCS at a cell concentration of $2-4 \times 10^6$ per ml.

Primary EBA antibodies (bound to epithelial cells) were isolated on magnetic, Dynabeads (Dynal International, Oslo Norway) as follows. Dynabeads M-450 were coated with a secondary antibody (sheep-antimouse, by the manufacturer). The beads were first washed twice for 5 minutes at 2°–8° C. in phosphate buffered saline (PBS), pH 7.4, containing 0.1% FCS. The Dynabeads were collected using a magnet and the supernatant was discarded and the beads resuspended in equivalent initial volume.

The Dynabeads coated with the secondary anti-murine antibody at a ratio of 5 particles per target cell were added to the sputum sample. The concentration should be about $10^7$ beads per ml of solution. The mixture was incubated for 30 minutes at 4° C. on a Rock-N-Roller. Cold (4°–8° C.) HBSS with 1% FCS was added in a volume at least 4x the volume of the bead/cell suspension. The Dynabeads were concentrated using the magnet. The supernatant was removed and the beads washed thoroughly 3 times using HBSS/1% FCS in a volume equal to that above (at least 4x the volume of the bead/cell suspension). The Dynabead/cell suspension was centrifuged at 1,000× g and resuspended in SDS/Proteinase K and DNA isolated for PCR.

B. PCR AMPLIFICATION

1. For k-ras, amplify 120 bp DNA fragment:

| | |
|---|---|
| Sputum DNA | 5 ul |
| Distilled water | 34 ul |
| PCR buffer(10 ×) | 5 ul |
| dNTP | 3 ul |
| Primer Kras 1 | 1 ul |
| Primer Kras 1 as | 1 ul |
| Taq(polymerase, 5 U/ul) | 1 ul |

Primer Kras 1 = 5'-AGGAATTCATGACTGAATATAAACTTGT-3' (SEQ. ID NO. 1);
Kras 1 AS = 5'-ATCGAATTCTATGCATATTAAAACAAGATT-3' (SEQ. ID NO. 2).

The sample was placed in a 500 ul tube to which 2 drops of mineral oil were added. The sample was amplified in an Omnigene PCR machine, as follows: 95° C. for 30 sec.; 55° C. for 1 min. 35 cycles; 70° C. for 1 min.; and 70° C. for 5 min. 1 cycle.

2. For p53 (exons 4–5), amplify 500 bp DNA fragment:

| | |
|---|---|
| Sputum DNA | 5 ul |
| Distilled water | 34 ul |
| PCR buffer(10 ×) | 5 ul |
| dNTP | 3 ul |
| Primer 5S | 1 ul |
| Primer Int-6AS | 1 ul |
| Taq(polymerase, 5 U/ul) | 1 ul |

Primer 5S = 5'-GTAGGAATTCACTTGTGCCCTGACTT-3' (SEQ. ID NO. 3);
Primer Int-6AS = 5'-CATCGAATTCCACTGACAACCACCCTT-3' (SEQ. ID NO. 4).

The sample was placed in a 500 ul tube to which 2 drops of mineral oil were added. The sample was amplified in an Omnigene PCR machine, as follows: 95° C. for 30 sec.; 60° C. for 1 min., 35 cycles; 70° C. for 1 min.; and 70° C. for 5 min., 1 cycle.

3. For p53 (exons 6–7), amplify 750 bp DNA fragment:

| | |
|---|---|
| Sputum DNA | 5 ul |
| Distilled water | 34 ul |
| PCR buffer(10 ×) | 5 ul |
| dNTP | 3 ul |
| Primer 7S | 1 ul |
| Primer 8AS | 1 ul |
| Taq(polymerase, 5 U/ul) | 1 ul |

Primer 7S AS = 5'-GTAGGAATTCCAAGGCGCACTGGCCTC-3' (SEQ. ID NO. 5);
Primer 8 AS = 5'-ACTGAATTCTTCGTCTCCTCCACCGC-3' (SEQ. ID NO. 6).

The sample was placed in a 500 ul tube to which 2 drops of mineral oil were added. The sample was amplified in an Omnigene PCR machine, as follows: 95° C. for 30 sec.; 60° C. for 1 min., 35 cycles; 70° C. for 1 min.; and 70° C. for 5 min., 1 cycle.

All amplifications performed with negative control (water devoid of any DNA) and positive (cell line DNA) controls, such as SW480 (12 val mutation K-ras) or DZ74 (273 cys mutation p53).

C. CLONING

To 5 ul of the PCR product above, 5ul of 2× stop buffer (Bromophenol blue in Ficoll, glycerol and sarcosyl with tris-acetate buffer) was added. The samples were run on 1% or 2% agrose gels to observe the yield of amplification. The remaining 45 ul of the PCR product, was mixed with 155 ul distilled water. To the 200 ul PCR mixture, 200 ul PC-9, was added and vortexed well. The tube was spun for 2 min. in Hermle Z230 M table centrifuge at high speed. The supernatant was removed to another tube and the pellet was treated with PC-9 one more time.

The supernatant was removed to a new 1.5 ml tube and 66 ul 10M ammonia acetate, 2 ul glycogen and 660 ul 200 proof ethanol were added and the tube was vortexed well. The tube was spun for 20 min. in a Hermle Z230 M table centrifuge at high speed. The supernatant was decanted and 660 ul 70% ethanol, was added and the solution mixed. The tube was spun for 2 more minutes and decanted again. The sample was dried in a HETOVAC.

DNA was resuspended by adding 4 to 8 ul of distilled water depending on the size of the pellet. Two ul of DNA was mixed with 1 ul T4 Lamda Zap I, (Stratagene, La Jolla, Calif.) 1 ul standard T4 ligation buffer (5×). The DNA mixture was incubated at 65° C. for 5 min., 37° C. for 5 min. and 24° C. for 5 min. in a water bath. One ul of T4.ligase was added and the mixture was incubated at 15° C. for 4 to 6 hours. One ul of the ligated product was mixed with 2.4 ul packaging extract (Stratagene, La Jolla, Calif.) (Red) and 3.75 ul packaging extract (Yellow). The ligation mixture was kept at room temperature for 2 hours. 250 ul phage dilution buffer (stock phage) was added to the mixture after 2 hours. About 10 ul to 100 ul stock phage were added to 100 ul XL1-B cells and incubated at 37° C. for 10 min. 4 ml of 55° C. top agarose was added and the mixture was plated on L-Agar gel plates at 37° C. overnight.

D. HYBRIDIZATION

A piece of nylon hybridization transfer membrane Zetaprobe (BioRad Richmond, Calif.) was laid on the surface of the gel which contains lysis plaques for 1 min. The membrane was then transferred to on a blot paper soaking 0.5M NaOH, plaque side up for 15 min. The membrane was then rinsed in 2× SSC for 5 min. twice. The membrane was then placed on a blot paper before crosslinking under UV light for 30 seconds. The membranes were then placed in plastic bags for hybridization.

Oligimers (Table 1) were radioactively labeled using $^{32}P$ γ-ATP by standard methods (T4 kinase). The labelled probes were added to bags containing plaque lifts. Hybridization was performed at the temperature which is 10° C. below the melting temperature of the probe for 1 hour in a shaking bath. The membranes were then removed and washed in 3× SSC/0.1% SDS at room temperature for 5 min. and in 3× SSC/0.1% SDS at the melting temperature of the probe for 30 min. The excess solution was removed from the membrane before wrapping in Saran Wrap. The membranes were exposed at −80° C. for 4 hours or overnight.

TABLE 1

Oligomers Used In Sputum Detection

SEQ. ID NO.:

Oligomers used in detection of p53 gene mutations 15. 5'-CAC AGC CCC TCC CTG G-3' (codon 89 del 1 C) Melting T. 56° C.
16. 5'-TCT GGG CTG CTT GCA TTC-3' (codon 113 TTC to TGC) MT. 56° C.
17. 5'-GCC AAC TGC CCA AGA CC-3' (codon 138 GCC to CCC) MT. 56° C.
18. 5'-GCC CTG TGT AGC TGT GG-3' (codon 144 CAG to TAG) MT. 56° C.
19. 5'-GCA GCT GTG AGT TGA TTC-3' (codon 146 TGG to TGA) MT. 54° C.
20. 5'-TTC CAC ACA CCC GCC CG-3' (codon 151 CCC to CAC) MT. 58° C.
21. 5'-CCC GCC CGT CAC CCG C-3' (codon 154 GGC to GTC) MT. 60° C.
22. 5'-GCA CCC GCT TCC GCG C-3' (codon 157 GTC to TTC) MT. 58° C.
23. 5'-CCG CGT CCT CGC CAT G-3' (codon 158 CGC to CTC) MT. 56° C.
24. 5'-CGT CCG CGT CAT GGC C-3' (codon 159 GCC to GTC) MT. 56° C.
25. 5'-CGC CAT GGA CAT CTA CA-3' (codon 161 GCC to GAC) MT. 52° C.
26. 5'-CGC CAT GAC CAT CTA CA-3' (codon 161 GCC to ACC) MT. 52° C.
27. 5'-ACA TGA CGT AGG TTG TGA-3' (codon 171 GAG to TAG) MT. 52° C.
28. 5'-CGG AGG TTT TGA GGC GC-3' (codon 173 GTG to TTG) MT. 56° C.
29. 5'-TTG TGA GGC ACT GCC CC-3' (codon 175 CGC to CAC) MT. 56° C.
30. 5'-TTG TGA GGC TCT GCC CC-3' (codon 175 CGC to CTC) MT. 56° C.
31. 5'-AGG CGC TGG CCC CAC C-3' (codon 176 TGC to TGG) MT. 58° C.
32. 5'-AGG CGC TAC CCC CAC C-3' (codon 176 TGC to TAC) MT. 56° C.
33. 5'-AGG CGC TTC CCC CAC C-3' (codon 176 TGC to TTC) MT. 56° C.
34. 5'-CCC CCA CTA TGA GCG CT-3' (codon 179 CAT to TAT) MT. 56° C.
35. 5'-CCC CAC CAG GAG CGC T-3' (codon 179 CAT to CAG) MT. 56° C.
36. 5'-CCC CAC CGT GAG CGC T-3' (codon 179 CAT to CGT) MT. 56° C.
37. 5'-CCC CCA CGA TGA GCG C-3' (codon 179 CAT to GAT) MT. 56° C.
38. 5'-TCA GCA TCG TAT CCG AG-3' (codon 194 CTT to CGT) MT. 52° C.

5,561,041

TABLE 1-continued

Oligomers Used In Sputum Detection

SEQ. ID NO.:

39. 5'-ATC CGA GTG TAA GGA AAT T-3' (codon 198 GAA to TAA) MT. 52° C.
40. 5'-CGA GTG GAA GAA AAT TTG C-3' (codon 199 GGA to GAA) MT. 54° C.
41. 5'-TGT GGA GTG TTT GGA TGA-3' (codon 205 TAT to TGT) MT. 52° C.
42. 5'-TGG ATG ACT GAA ACA CTT T-3' (codon 209 AGA to TGA) MT. 52° C.
43. 5'-ACA CTT TTT GAC ATA GTG T-3' (codon 213 CGA to TGA) MT. 50° C.
44. 5'-ACA CTT TTC CAC ATA GTG T-3' (codon 213 CGA to CCA) MT. 52° C.
45. 5'-CAC TTT TCG ACG TAG TGT G-3' (codon 214 CAT to CGT) MT. 56° C.
46. 5'-TTT TCG ACA TAT TGT GGT G-3' (codon 215 AGT to ATT) MT. 52° C.
47. 5'-ATA GTG TGT TGG TGC CCT-3' (codon 217 GTG to TTG) MT. 54° C.
48. 5'-GGT GCC CTG TGA GCC G-3' (codon 220 TAT to TGT) MT. 56° C.
49. 5'-CCG CCT GAC GTC TGG TT-3' (codon 224 GAG to GAC) MT. 56° C.
50. 5'-TCT GAC TGA ACC ACC ATC-3' (codon 229 TGT to TGA) MT. 54° C.
51. 5'-CAT CCA CTG CAA CTA CAT-3' (codon 234 TAC to TGC) MT. 52° C.
52. 5'-CAA CTA CAT ATG TAA CAG TT-3' (codon 237 ATG to ATA) MT. 52° C.
53. 5'-ACT ACA TGT TTA ACA GTT CC-3' (codon 238 TAT to TTT) MT. 54° C.
54. 5'-ACT ACA TGT GAA ACA GTT CC-3' (codon 238 TAT to TGA) MT. 56° C.
55. 5'-CAG TTC CTC CAT GGG CG-3' (codon 242 TGC to TCC) MT. 56° C.
56. 5'-CAG TTC CTT CAT GGG CG-3' (codon 242 TGC to TTC) MT. 54° C.
57. 5'-CAG TTC CTG GAT GGG CG-3' (codon 242 TGC to TGG) MT. 56° C.
58. 5'-CCT GCA TGT GCG GCA TG-3' (codon 244 GGC to TGC) MT. 56° C.
59. 5'-GCA TGG GCT GCA TGA AC-3' (codon 245 GGC to TGC) MT. 54° C.
60. 5'-GCA TGG GCG ACA TGA AC-3' (codon 245 GGC to GAC) MT. 54° C.
61. 5'-GGC GGC ATC AAC CGG AG-3' (codon 246 ATG to ATC) MT. 58° C.
62. 5'-GGC ATG ATC CGG AGG CC-3' (codon 247 AAC to ATC) MT. 58° C.
63. 5'-CAT GAA CCT GAG GCC CAT-3' (codon 248 CGG to CTG) MT. 56° C.
64. 5'-GCA TGA ACT GGA GGC CCA-3' (codon 248 CGG to TGG) MT. 58° C.
65. 5'-GCA TGA ACC AGA GGC CCA-3' (codon 248 CGG to CAG) MT. 58° C.
66. 5'-AAC CGG AGT CCC ATC CTC-3' (codon 249 AGG to AGT) MT. 58° C.
67. 5'-AAC CGG AGC CCC ATC CT-3' (codon 249 AGG to AGC) MT. 56° C.
68. 5'-AAC CGG ATG CCC ATC CTC-3' (codon 249 AGG to ATG) MT. 58° C.
69. 5'-GAA CCG GGG GCC CAT C-3' (codon 249 AGG to GGG) MT. 56° C.
70. 5'-TCA CAC TGT AAG ACT CCA-3' (codon 258 GAA to TAA) MT. 52° C.
71. 5'-TCA CAC TGA AAG ACT CCA-3' (codon 258 GAA to AAA) MT. 52° C.
72. 5'-CAC TGG AAG TCT CCA GGT-3' (codon 259 GAC to GTC) MT. 56° C.
73. 5'-TAA TCT ACC GGG ACG AAA-3' (codon 265 CTG to CCG) MT. 54° C.
74. 5'-TAA TCT ACC TGG ACG AAA-3' (codon 265 CTG to CCT) MT. 52° C.
75. 5'-TCT ACT GGT ACG AAA CAG-3' (codon 266 GGA to GTA) MT. 54° C.
76. 5'-ACT GGG ACC GAA CAG CTT-3' (codon 267 CGG to CCG) MT. 54° C.
77. 5'-GCT TTG AGC TGC GTG TTT-3' (codon 272 GTG to CTG) MT. 54° C.
78. 5'-GCT TTG AGG AGC GTG TTT-3' (codon 272 GTG to GAG) MT. 54° C.
79. 5'-TTG AGG TGC TTG TTT GTG-3' (codon 273 CGT to CTT) MT. 52° C.
80. 5'-TTG AGG TGT GTG TTT GTG-3' (codon 273 CGT to TGT) MT. 52° C.
81. 5'-TTG AGG TGC ATG TTT GTG-3' (codon 273 CGT to CAT) MT. 52° C.
82. 5'-TTG AGG TGC CTG TTT GTG-3' (codon 273 CGT to CCT) MT. 54° C.
83. 5'-AGG TGC GTG GTT GTG CCT-3' (codon 274 GTT to GGT) MT. 58° C.
84. 5'-GCG TGT TTA TGC CTG CCT-3' (codon 275 TGT to TAT) MT. 56° C.
85. 5'-GCG TGT TTT GCC CTG CCT-3' (codon 275 TGT to TTT) MT. 56° C.
86. 5'-TTG TGC CTT TCC TGG GAG-3' (codon 277 TGT to TTT) MT. 56° C.
87. 5'-TGC CTG TCT TGG GAG AGA-3' (codon 278 CCT to CTT) MT. 56° C.
88. 5'-TGC CTG TTC TGG GAG AGA-3' (codon 278 CCT to TCT) MT. 56° C.
89. 5'-TGC CTG TCG TGG GAG AGA-3' (codon 278 CCT to CGT) MT. 58° C.
90. 5'-TCC TGG GAT AGA CCG GCG-3' (codon 280 AGA to ATA) MT. 58° C.
91. 5'-TGG GAG ATA CCG GCG CAC-3' (codon 281 GAC to TAC) MT. 58° C.
92. 5'-GAG AGA CCC GCG CAC AG-3' (codon 282 CGG to CCG) MT. 58° C.
93. 5'-GAG AGA CGG GCG CAC AG-3' (codon 282 CGG to GGG) MT. 58° C.
94. 5'-GAG AGA CTG GCG CAC AG-3' (codon 282 CGG to TGG) MT. 56° C.
95. 5'-AGA CCG GCC CAC AGA GG-3' (codon 283 CGC to CCC) MT. 58° C.
96. 5'-AGA CCG GGG CAC AGA GG-3' (codon 283 CGC to GGC) MT. 58° C.
97. 5'-CCG GCG CCC AGA GGA A-3' (codon 284 ACA to CCA) MT. 56° C.
98. 5'-GCG CAC AAA GGA AGA GAA-3' (codon 285 GAG to AAG) MT. 54° C.
99. 5'-CAC AGA GGG AGA GAA TCT-3' (codon 286 GAA to GGA) MT. 54° C.
100. 5'-ATC TCC GCT AGA AAG GGG-3' (codon 291 AAG to TAG) MT. 56° C.
101. 5'-GCA AGA AAG GGA GCC TC-3' (codon 293 del 1 G) MT. 54° C.
102. 5'-CTC ACC ACT AGC TGC CC-3' (codon 298 GAG to TAG) MT. 56° C.
103. 5'-GAT GTT CTG AGA GCT GAA-3' (codon 342 CGA to TGA) MT. 52° C.
104. 5'-GAT GTT CCA GAG CTG AAT-3' (codon 342 del 1 G) MT. 52° C.
105. 5'-GGC CTT GAA CTC AAG GAT-3' (codon 349 del 1 G) MT. 54° C.
106. 5'-CTG GGA GAC ACC GGC G-3' (codon 281 GAC to CAC) MT. 56° C.
107. 5'-ACC GGA GGT TCA TCC TC-3' (codon 250 CCC to TTC) MT. 54° C.
108. 5'-CAT GTG TAA ACA GTT CCT G-3' (codon 239 ins 1 A) MT. 54° C.
109. 5'-AGC ATC TTA ATC CGA GTG-3' (codon 195 ins 1 A) MT. 52° C.
110. 5'-GTC TGG CCC TCC TCA GC-3' (codon 191 del 1 C) MT. 58° C.
111. 5'-GCT GCC CCC CAC CAT GA-3' (codon 178 ins 1 C) MT. 58° C.
112. 5'-CCG CGT CGC GCC ATG-3' (codon 158 del 1 C) MT. 54° C.
113. 5'-AGA CCT GCC TGT GCA GC-3' (codon 142 del 1 C) MT. 56° C.

TABLE 1-continued

Oligomers Used In Sputum Detection

SEQ. ID NO.:

114. 5'-CCT GTC CTT GGG AGA GA-3' (codon 279 ins 1 T) MT. 54° C.

Oligomers used in detection of ras gene mutations 115. 5'-GGAGCTGTTGGCGTAGGCAA-3' (Val$^{12}$),
116. 5'-GGAGCTGATGGCGTAGGCAA-3' (Asp$^{12}$),
117. 5'-GGAGCTAGTGGCGTAGGCAA-3' (Ser$^{12}$),
118. 5'-GGAGCTTGTGGCGTAGGCAA-3' (Cys$^{12}$), (Boyle, et al., Can. Res. 53 (19):4477, 1993; Hollstein, et al., Science 253:49, 1991; Somers, et al., Can. Res. 52:5997, 1992; Sakai, et al., Oncogene, 7:972, 1992).

E. HYBRIDIZATION AND DETECTION

Alternatively, the oligomers were labeled using chemiluminescence. 100 pmoles of oligomers was added to 16 ul cacodylate buffer, 10 ul fluorescein-dUDP, 16 ul terminal transferase and water to total 160 ul. The mixture was incubated for 1 hour at 37° C.

Membranes were pre-hybridized for 1 hour in [5× SSC/ 0.02% SDS and 0.5% (W/V) blocking agent (milk) (Amersham, UK)]. The probe was added and hybridization was allowed to go for 1 hour at the temperature which is 10° C. below the melting temperature of the probe in shaking bath. The membranes were washed in 3× SSC/0.1% SDS at room temperature 5 min. twice. The membranes were then washed in 3× SSC/0.1% SDS at the melting temperature of the probe for 15 min. three times in the washing bath. The membranes were then rinsed (NaCl, 0.15 mol/lit Tris buffer, 0.1 mol/lit, pH7.5) for 1 minute followed by incubation in block buffer (5% dry nonfat milk/TBS) for 30 min. The membranes were then rinsed in TBS for 1 min. and incubated in antibody solution (1:5000 anti-fluorescein alkaline phosphatase antibody (Boehringer Manheim) in 5% milk/TBS) for 30 minutes. The membrane was then washed in TBS for 5 min. eight times with shaking. The detection reagent, lumigen PPD (Boerhinger Manheim 1:100 in MgCl$_2$,50 mmol/lit/ TBS, pH 9.5) were mixed, and the blots incubated in the solution for 1 min. The extra solution was removed and the membrane wrapped with plastic and exposed to X-ray film immediately for 10 to 60 minutes.

EXAMPLE 2

Paraffin embedded primary lung tumor samples from 15 patients who went on to develop adenocarcinoma of the lung during the JHLP trial were studied (Table 1). Patients were chosen based on the availability of paraffin embedded tissue following surgical resection and negative sputum cytology prior to definitive diagnosis. Following extraction of tumor DNA, a segment of two target genes from these primary carcinoma samples was amplified through PCR in order to detect mutations in the k-ras oncogene and p53 tumor suppressor gene. Adenocarcinomas were chosen because these tumors have a higher incidence of k-ras mutations (30%) than other lung tumors (Rodenhuis, et al., *Can Res* 48:5738–5741, 1988; Rodenhuis, S & Slebos, RJ, *Am Rev Res Dis* 142:S27–S30, 1990). p53 gene mutations were examined as these are the most common genetic alterations found in these tumors and a variety of other cancers (Takahashi, et al., *Science* 246:491–494, 1989; Kishimoto, et al., *Can Res* 52:4799–4804, 1992; Hollstein, et al., *Science* 253:49–53, 1991). Sequence analysis of the PCR products from the two target genes identified 10 primary tumors which contained either a k-ras or p53 gene mutation (Table 2). The k-ras mutations were those commonly associated with adenocarcinoma of the lung and occurred predominantly at codon 12. The two p53 mutations occurred at codons 273 and 281, and both were previously described in lung cancers (Takahashi, et al., supra; Kishimoto, et al., supra; Hollstein, et al., supra). Many tumor samples were small (<1 cm) and DNA was insufficient for extensive sequence analysis of p53 (exons 5 to 8) in all tumors.

Following identification of tumors with oncogene mutations, all of the available corresponding sputum samples from these affected patients were obtained. None of the patients that were analyzed ever had a positive sputum cytology in the JHLP study. Therefore, all but one of the patients (L4 evaluated because of cough) were diagnosed by chest x-ray.

Those sputum samples that were available, (generally one or two samples prior to clinical diagnosis) were analyzed by a PCR-based assay able to detect one mutant containing cell among an excess background of 10,000 normal cells (Sidransky, D., et al, *Science*, 252:706–709, 1991; Sidransky, D., et al., *Science* 256:102–105, 1992). This assay was based on the amplification of sputum DNA, followed by cloning into a phage vector and transfer to nylon membranes as described in Example 1. A mutant-specific oligomer was hybridized to each of the filters to identify specific point mutations in either the k-ras or p53 gene present in sputum. Neoplastic cells harboring either ras or p53 mutations were detected in sputum from eight of the 10 patients who had tumors containing oncogene mutations. Positive sputum samples harboring a clonal population of cancer cells were obtained from one to 13 months prior to clinical diagnosis (Table 2). Detection of one cancer cell among 160 normal cells (1/320÷2=160; each normal cell contributes 2 wildtype alleles) was detected in sputum from Patient L4 thirteen months prior to his clinical diagnosis (Table 2). The tumor from this patient contained >95% positive plaques when probed with a mutant-specific codon 273 oligomer for p53 and his sputum sample also contained several positive plaques (FIG. 1). Many clones with a PCR insert from the p53 gene hybridized to an oligomer probe specific for the codon 273 Arg→His mutation in the patient's (L4) tumor (T). A fewer number of clones hybridized to the same specific probe in the patients sputum(S). There were no hybridizing clones to this probe in a control sputum from a patient (L15) without a p53 gene mutation in his primary lung cancer (C). Stored sputum samples in 30 cc screw top glass bottles containing 2% carbowax/50% alcohol (Saccomanno's fixative) preservative solution were located [details on collection of samples in (Berlin, NI, Buncher, CR, Fontana, RS, Frost, JK & Melamed, MR, *Am Rev Resp Dis* 130:545–549, 1984; Tockman, MS, *Chest* 89:324S–325S, 1986; Tockman, MS, et al., *J Clin Oncol* 6:1685–1693, 1988)]. 5 cc was removed from each (approx. 50,000–500,000 cells), spun at ×1,000 g for 5-mins. and rehydrated in 5 cc of normal saline. Cells were then respun ×1,000 g and resuspended in 1 ml of 1% SDS/proteinase k (5 mg/µl was used for each PCR reaction performed in a separate PCR dedicated room to eliminate possibility of contamination. Primers from k-ras and p53 contained EcoRI sites to facilitate cloning. Following 35 cycles of amplification, products were cleaved with EcoRI and ligated to lamda Zap II (Stratagene) (Sidransky, D., et al., Science 256:102–105, 1992). XLI cells infected with bacteriophage were plated on L-Agar at a density of 500–3,000 plaques per plate, transferred to nylon membranes and hybridized with oligonucleotides used for hybridizations were labelled with $^{32}p$ and hybridized as in (Sidransky, D., et al., Science 252:706–709, 1991; Sidransky, et al, 1992, Supra). Oligonucleotides used for detection included: 5'-GGAGCTGGTGGCGTAG-GCAA-3' for WT ras (SEQ. ID NO. 119), 5'-GGAGCTGT-TGGCGTAGGCAA-3' for the $Val^{12}$ mutant (SEQ. ID NO. 115), 5'-GGAGCTGATGGCGTAGGCAA-3' for the $Asp^{12}$ mutant (SEQ. ID NO. 116), 5'-GGAGCTAGTGGCGTAG-GCAA-3' for the $Ser^{12}$ mutant (SEQ. ID NO. 117), 5'-GGAGCTTGTGGCGTAGGCAA-3' for the $Cys^{12}$ mutant (SEQ. ID NO. 118), 5'-ATGGGCGCCATGAAC-CGG-3' for WT p53 (SEQ. ID NO. 120), 5'-TTGAGGTG-CATGTTTGTG-3' for the $His^{273}$ mutant (SEQ. ID NO. 121), and 5'-TGGGAGAGGCCGGCGCA-3' for the $Gly^{281}$ mutant (SEQ. ID NO. 122).

Figure 2:
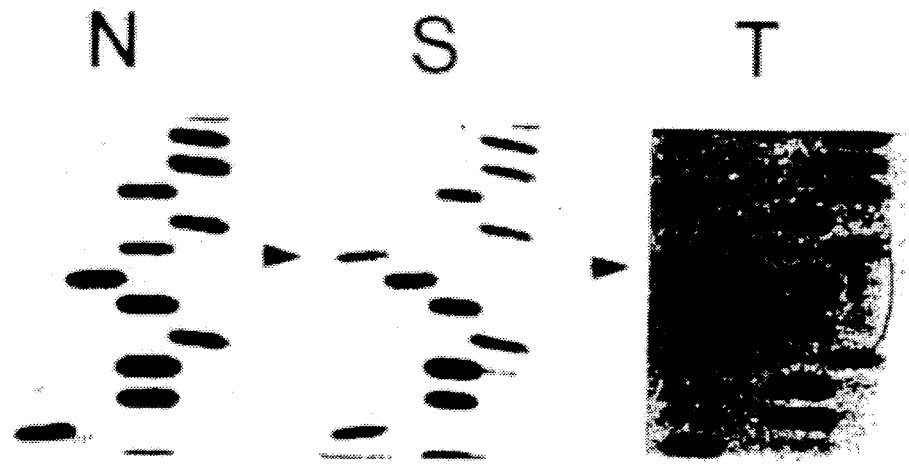
FIG. 2 shows sequencing gels of clones which contained the p53 normal and mutant sequences. The wild type sequence is seen in normal (N) control and the 273 CGT->CAT (Arg->His) mutant sequence (arrow) in the tumor (T) with a residual wild type band. The same mutant band is seen in sputum (S) as that found in the primary tumor.

To verify identification of the codon 273 mutation in the sputum, a positive plaque from the sputum assay was picked and sequenced confirming presence of the same mutation (FIG. 2). Sequencing gels of pooled clones for p53 show the WT sequence in a normal (N) control and the 273 CGT→CAT (Arg→His) mutant sequence (arrow) in the tumor (T) with a residual WT band. One positive plaque depicted in FIG. 1(S) was picked and sequenced revealing the same mutant band in sputum (S) as that found in the primary tumor. In each panel, the lanes represent A, C, G, and T terminations from left to right. Briefly, tumor DNA was extracted from paraffin slides by incubation in xylene, followed by treatment with SDS/proteinase k and ethanol precipitation. Exon 1 of the K-ras gene and exons 5 to 8 of p53 (if sufficient DNA available were amplified by PCR, cloned into Lamda Zap II (Stratagene) and sequenced as described (Sidransky, et al., 1991, supra). However, the p53 gene was amplified in two segments utilizing the following primers: p53-5S 5'-GTAGGAATTCACTTGTGCCCT-GACTT-3' (SEQ. ID NO. 3) and p53-6AS 5'-CATCGAAT-TCCACTGACAAOCACCCTT-3' (SEQ. ID NO. 4) (exons 5–6); p53-7S 5'-GTAGGAATTCCAAGGCGCACTGGC-CTC-3' (SEQ. ID NO. 5) and p53-8AS 5'-ACTGAATTCT-TCGTCTCCTCCACCGC-3' (SEQ. ID NO. 6) for exons 7–8.

In positive sputum samples, the ratio of cancer to normal cells ranged from one in 600 (Patient L5) to 1 in 50 (Patient L3), with the majority of sample containing approximately one cancer cell among 150 normal cells. Five control patients with lung cancer whose tumors did not contain either a k-ras (codons 12 and 13) or p53 (exons 5 to 8) gene mutation by sequence analysis were negative by this assay for all twelve k-ras and both p53 mutant-specific probes.

In two patients, both of whom had only a single sputum sample available a clonal population of mutant-containing cells was undetectable despite the presence of mutations in their primary tumors (Table 2). Furthermore, the first emergence of a clonal population of cancer cells in positive patients was untraceable by this sputum assay because of missing samples prior to diagnosis. However, in six of the 10 patients, sputum samples were available >24 months prior to diagnosis and were negative. This suggests a limit of 13 to 24 months for molecular diagnosis by our assay prior to clinical presentation. As a further control, 6/8 patients who initially tested positive, were found to test negative in sputum samples obtained following complete surgical resection of their tumor. There did not appear to be any correlation between the site of the tumor and the ability to detect mutations in sputum samples by this assay. "False negative" samples may be due to inappropriate collection, poor cellular content or to the variable presence of tumor cells in sputum. Information gained from cytological diagnosis in sputum through routine light microscopy has previously suggested that examination of two or three samples may improve the diagnostic yield significantly, and this likely pertains to molecular diagnosis as well.

Patient L4 with a large $T_3$ lesion had the longest interval (13 months) from sputum detection to diagnosis. He also had a negative transthoracic biopsy six months prior to definite diagnosis because a small lesion was noted on chest x-ray. This patient thus had two opportunities for routine cytopathologic detection prior to clinical diagnosis. He died of metastatic disease four months following surgical resection. This particular case serves to illustrate the limitations of routine cytology and the ability to augment morphologic analysis through the use of probes for specific gene mutations.

TABLE 2

| | | | | | | | |
|---|---|---|---|---|---|---|---|
| | | | | | LUNG CANCER PATIENTS WITH GENE MUTATION ANALYSIS OF SPUTUM | | |
| Patient | | Tumor | Tumor | Tumor | MUTATIONS FOUND IN SPUTUM | | |
| Number | Age/Sex | Location # | Type/State* | Mutations | Pre-Dx (Mon.) | Ratio (M/T) | Post-Op |
| L1 | 65/M | RUL | A./T1, N0, MO | Kras-12Ser | 3 | 1/270 | Negative |
| L2 | 57/M | LUL | A./T2, N1, MO | Kras-12Asp | 1 | 1/300 | N/A |
| L3 | 63/M | RUL | A./T1, N0, MO | Kras-12Val | 4 | 1/100 | Negative |
| L4 | 51/M | LUL | A./T3, N0, MO | p53-273His | 13 | 1/320 | N/A |
| L5 | 67/M | LUL | A./T1, N0, MO | Kras-12Cys | 1 | 1/1200 | Negative |
| L6 | 67/M | RUL | A./T3, N0, MO | p53-281Gly | Negative | 0 | Negative |
| L7 | 70/M | RUL | A./T1, N0, MO | Kras-12Cys | 1 | 1/220 | Negative |
| L8 | 59/M | RUL | A./T1, N0, MO | Kras-12Cys | 1 | 1/170 | Negative |
| L9 | 48/M | RUL | A./T1, N0, MO | Kras-12Val | Negative | 0 | Negative |
| L10 | 63/M | RLL | A./T1, N0, MO | Kras-12Cys | 1 | 1/330 | Negative |
| L11 | 60/M | RUL | A./T3, N1, MO | None | Negative | 0 | ND |
| L12 | 56/M | LLL | A./T1, N0, MO | None | Negative | 0 | ND |

TABLE 2-continued

LUNG CANCER PATIENTS WITH GENE MUTATION ANALYSIS OF SPUTUM

| Patient Number | Age/Sex | Tumor Location # | Tumor Type/State* | Tumor Mutations | MUTATIONS FOUND IN SPUTUM | | |
|---|---|---|---|---|---|---|---|
| | | | | | Pre-Dx (Mon.) | Ratio (M/T) | Post-Op |
| L13 | 65/M | RUL | A./T1, N0, M0 | None | Negative | 0 | ND |
| L14 | 61/F | RUL | A./T2, N0, M0 | None | Negative | 0 | ND |
| L15 | 62/M | LUL | A./T2, N0, M0 | None | Negative | 0 | ND |

A.: adenocarcinoma
L: Large cell carcinoma
Pre-Dx: months prior to actual clinical diagnosis
Op: operation N/A: Not available
ND: not done
M/T: number of mutant alleles/Total plaques with target gene insert.
RUL: right upper lobe;
LUL: left upper lobe;
RLL: right lower lobe;
LLL: left lower lobe, of the lung.
*Staging system is according to the ASCC (Mountain CF., Chest, 89:225S–233S, 1986). All sputum samples for Patients L1 to L10 were reamplified, recloned, and the assay repeated for verification.

The results of these experiments provide an embodiment wherein successful detection of neoplasia was accomplished and provides a practical basis for a new approach for detecting the presence of neoplasias, such as lung tumors, in a non-invasive fashion. The approach would have utility in monitoring patient populations and treatments designed to minimize the incidence of neoplasia. It also could be used in screening asymptomatic patients, especially those at risk by virtue of inherited or environmental factors, for the presence of neoplasia. The current results indicate that a significant fraction of early lung cancers and dangerous pre-malignant lesions can be identified through this strategy. Additionally, these findings indicate that other mutant nucleotide sequences, besides K-ras and p53, which are associated or indicative of lung neoplasias, would also be detectable in sputum specimens.

The foregoing is meant to illustrate, but not to limit, the scope of the invention. Indeed, those of ordinary skill in the art can readily envision and produce further embodiments, based on the teachings herein, without undue experimentation.

SUMMARY OF SEQUENCES

SEQ ID NO's: 1–2 are nucleotide sequences for oligonucleotide primers which hybridze to flanking regions of mutant K-ras sequences.

SEQ ID NO's: 3–4 are nucleotide sequences for oligonucleotide primers which hybridize to flanking regions of mutant p53 sequences in exons 5–6.

SEQ ID NO's: 5–6 are nucleotide sequences for oligonucleotide primers which hybridize to flanking regions of mutant p53 sequences in exons 7–8.

SEQ ID NO: 7 is the nucleotide sequence for mutant nucleotides in K-ras at $Val^{12}$ position.

SEQ ID NO: 8 is the nucleotide sequence for mutant nucleotides in K-ras at $Asp^{12}$ position.

SEQ ID NO: 9 is the nucleotide sequence for mutant nucleotides in K-ras at $Ser^{12}$ position.

SEQ ID NO: 10 is the nucleotide sequence for mutant nucleotides in K-ras at $Cys^{12}$ position.

SEQ ID NO's: 11–12 are the nucleotide sequence for mutant nucleotides in p53 at codons 273 and 281, respectively.

SEQ ID NO's: 13–14 are the nucleotide sequence for wild type K-ras and p53 to which the probes of the invention hybridize.

SEQ ID NO's: 15–114 are the nucleotide sequences for oligomers which are used to identify mutations in p53 in sputum samples.

SEQ ID NO's: 115–118 are the nucleotide sequence for ras gene mutant specific oligomers for $Val^{12}$, $Asp^{12}$, $Ser^{12}$ and $Cys^{12}$, respectively.

SEQ ID NO: 119 is the nucleotide sequence for an oligonucleotide used for detecting WT ras.

SEQ ID NO: 120 is the nucleotide sequence for an oligonucleotide used for detecting WT p53.

SEQ ID NO: 121 is the nucleotide sequence for an oligonucleotide used to detect the p53 mutation $His^{273}$.

SEQ ID NO: 122 is the nucleotide sequence for an oligonucleotide used to detect the p53 mutation $Gly^{281}$.

SEQ ID NO's: 123–128 are the nucleotide sequences for flanking regions of the target nucleic acid in p53 or ras to which specific oligonucleotides of the invention hybridize.

I claim:

1. A method for detecting the presence of a target mutant nucleotide sequence in a mammalian nucleic acid in a sputum specimen from a subject having or at risk of having a neoplastic disorder of the lung comprising:

a) isolating the nucleic acid present in the sputum specimen;

amplifying the nucleic; and (c) detecting the presence of the target mutant nucleotide sequence, wherein the presence of the target nucleotide sequence in the sputum is indicative of a neoplastic disorder of the lung.

2. The method of claim 1, wherein the amplification is by means of oligonucleotides which hybridize to the flanking regions of the target nucleic acid.

3. The method of claim 1, wherein the target nucleic acid comprises a mutation, a restriction fragment length polymorphism, a nucleic acid deletion, or a nucleic acid substitution.

4. The method of claim 3, wherein the mutation is associated with a neoplasm.

5. The method of claim 4, wherein the neoplasm is of the lung.

6. The method of claim 5, wherein the neoplasm is benign.

7. The method of claim 5, wherein the neoplasm is malignant.

8. The method of claim 1, wherein the target nucleic acid associated with the neoplasm is selected from the group consisting of an oncogene and a tumor suppressor gene.

9. The method of claim 8, wherein the oncogene is a member of the ras family.

10. The method of claim 9, wherein the oncogene is K-ras.

11. The method of claim 8, wherein the tumor suppressor gene is p53.

12. The method of claim 2, wherein the nucleotide sequence of the flanking regions to which the oligonucleotides hybridize is selected from 5'-ACAAGTTTATAT-TCAGTCATGAATTCCT-3' (SEQ. ID NO. 123), 5'-AATCTTGTTTTAATATGCATAGAATTCGAT-3' (SEQ. ID NO. 124), 5'-AAGTCAGGGCACAAGTGAATTC-CTAC-3' (SEQ. ID NO. 125), 5'-AAGGGTGGTTGT-CAGTGGAATTCGATG-3' (SEQ. ID NO. 126), 5'-GAG-GCCAGTGCGCCTTGGAATTCCTAC-3' (SEQ. ID NO. 127), or 5'-GCGGTGGAGGAGACGAAGAATTCAGT-3' (SEQ. ID NO. 128).

13. The method of claim 12, wherein the oligonucleotide is 5'-AGGAATTCATGACTGAATATAAACTTGT-3' (SEQ. ID NO. 1), 5'-ATCGAATTCTATGCATATTAAAACAA-GATT-3' (SEQ. ID NO. 2), 5'-GTAGGAATTCACTTGT-GCCCTGACTT-3' (SEQ. ID NO. 3), 5'-CATCGAATTC-CACTGACAACCACCCTT-3' (SEQ. ID NO. 4), 5'-GTAGGAATTCCAAGGCGCACTGGCCTC-3' (SEQ. ID NO. 5), or 5'-ACTGAATTCTTCGTCTCCTCCACCGC-3' (SEQ. ID NO. 6) and.

14. The method of claim 1, wherein the target nucleic acid is detected using a nucleic acid hybridization probe.

15. The method of claim 14, wherein the target nucleic acid to which the nucleic acid hybridization probe hybridizes is selected from 5'-TTGCCTACGCCAACAGCTCC-3'

(SEQ. ID NO. 7), 5'-TTGCCTACGCCATCAGCTCC-3' (SEQ. ID NO. 8), 5'-TTGCCTACGCCACTAGCTCC-3' (SEQ. ID NO. 9), 5'-TTGCCTACGCCACAAGCTCC-3' (SEQ. ID NO. 10), 5'-CACAAACATGCACCTCAA-3' (SEQ. ID NO. 11), 5'-TGCGCCGGCCTCTCCCA-3' (SEQ. ID NO. 12), 5'-CCGGTTCATGGCGCCCAT-3' (SEQ. ID NO. 14) or 5'-TTGCCCACGCCACCAGCTCC-3' (SEQ. ID NO. 13), and.

16. The method of claim 15 wherein the nucleic acid hybridization probe is selected from 5'-GGAGCTGTTG-GCGTAGGCAA-3' (SEQ. ID NO. 115), 5'-GGAGCT-GATGGCGTAGGCAA-3' (SEQ. ID NO. 116), 5'-GGAGCTAGTGGCGTAGGCAA-3' (SEQ. ID NO. 117), 5'-GGAGCTTGTGGCGTAGGCAA-3 (SEQ. ID NO. 118), 5'-TTGAGGTGCATGTTTGTG-3' (SEQ. ID NO. 121 ), 5'-TGGGAGAGGCCGGCGCA-3' (SEQ. ID NO. 122), 5'-ATGGGCGCCATGAACCGG-3' (SEQ. ID NO. 120), or 5'-GGAGCTGGTGGCGTAGGCAA-3' (SEQ. ID NO. 119), and.

17. A kit useful for the detection of a target mutant nucleic acid sequence from a sputum specimen from a subject having or at risk of having a neoplastic disorder of the lung, wherein the presence of the target mutant nucleic acid sequence in the sputum is indicative of the neoplastic disorder, the kit comprising carrier means being compartmentalized to receive in close confinement therein one or more containers comprising a first container containing a nucleic acid hybridization probe which hybridizes to the target nucleic acid wherein the target nucleic acid to which the probe hybridizes is selected from the group consisting of

5'-TTGCCTACGCCAACAGCTCC-3' (SEQ. ID NO. 7),

5'-TTGCCTACGCCATCAGCCC-3' (SEQ. ID NO. 8),

5'-TTGCCTACGCCACTAGCTCC-3' (SEQ. ID NO. 9),

5'-TTGCCTACGCCACAAGCTCC-3' (SEQ. ID NO. 10),

5'-CACAAACATGCACCTCAA-3' (SEQ. ID NO. 11),

5'-TGCGCCGGCCTCTCCCA-3' (SEQ. ID NO. 12),

5'-TTGCCCACGCCACCAGCTCC-3' (SEQ. ID NO. 13), and

5'-CCGGTTCATGGCGCCCAT-3'(SEQ. ID NO. 14): and a second container containing a means for detecting hybridization of the probe with the target nucleic acid.

18. The kit of claim 17, further comprising a container containing an oligonucleotide primer for amplification of the target nucleic acid.

19. The kit of claim 18, further comprising an amplification polymerase and deoxyribonucleotide(s).

* * * * *